United States Patent [19]
Batist et al.

[11] Patent Number: 5,352,809
[45] Date of Patent: Oct. 4, 1994

[54] 9-ALPHA-HYDROXY STEROIDS, PROCESS FOR THEIR PREPARATION, PROCESS FOR THE PREPARATION OF THE CORRESPONDING 9(11)-DEHYDRO DERIVATIVES AND PHARMACEUTICAL PREPARATIONS CONTAINING SUCH STEROIDS

[75] Inventors: Jacobus N. M. Batist, Kwintsheul; Arthur F. Marx, Delft; Willem J. van Zoest, Schiedam; Jagdish C. Kapur, Delft, all of Netherlands

[73] Assignee: Gist-Brocades N.V., Delft, Netherlands

[21] Appl. No.: 412,557

[22] PCT Filed: Oct. 9, 1987

[86] PCT No.: PCT/NL87/00026
§ 371 Date: Jul. 13, 1988
§ 102(e) Date: Jul. 13, 1988

[87] PCT Pub. No.: WO88/02753
PCT Pub. Date: Apr. 21, 1988

Related U.S. Application Data

[63] Continuation of Ser. No. 221,454, Jul. 13, 1988, abandoned.

[30] Foreign Application Priority Data

Oct. 10, 1986 [NL] Netherlands ............... 86201754
Jul. 13, 1987 [NL] Netherlands ............... 87201340

[51] Int. Cl.$^5$ ................................. C07J 1/00
[52] U.S. Cl. .......................... 552/610; 552/612
[58] Field of Search ........... 514/180; 552/562, 610, 552/612, 618; 540/97, 107

[56] References Cited

U.S. PATENT DOCUMENTS

| | | | |
|---|---|---|---|
| 2,837,545 | 6/1958 | Bernstein et al. | 552/562 |
| 2,840,580 | 6/1958 | Perlman et al. | 552/562 |
| 4,397,947 | 8/1983 | Marsheck et al. | 435/872 |
| 4,705,783 | 11/1987 | Crowe et al. | 514/180 |
| 4,921,638 | 5/1990 | Livingston et al. | 552/610 |

FOREIGN PATENT DOCUMENTS 565369 10/1958 Canada ............... 552/562

OTHER PUBLICATIONS

Eppstein, et al, JACS 80(7) 1958 pp. 3382 to 3389.

*Primary Examiner*—John M. Ford
*Assistant Examiner*—P. K. Sripada
*Attorney, Agent, or Firm*—Keck, Mahin & Cate

[57] ABSTRACT

New 9-alphahydroxy steroids are prepared by the introduction of substituents on the D-ring of 9-alpha-hydroxy-androst-4-ene-3,17-dione. The resulting compounds are useful intermediates in the synthesis of corticosteroids.

5 Claims, No Drawings

9-ALPHA-HYDROXY STEROIDS, PROCESS FOR THEIR PREPARATION, PROCESS FOR THE PREPARATION OF THE CORRESPONDING 9(11)-DEHYDRO DERIVATIVES AND PHARMACEUTICAL PREPARATIONS CONTAINING SUCH STEROIDS

This application is a continuation of application Ser. No. 07/221,454, filed Jul. 13, 1988 abandoned.

The invention relates to new 9-alpha-hydroxy steroids with a substituted D-ring, to their preparation and to the subsequent dehydration to 9,11-dehydro steroids.

Nearly all steroids which are currently used as pharmaceuticals originate either directly or indirectly from steroid raw materials found in nature. Originally diosgenin constituted the main supply of this raw material. In order to become less dependent of this specific compound one has investigated whether other steroids which are abundantly available, viz. cholesterol, sitosterol, stigmasterol and campesterol could also be used as starting material. Microbiological syntheses were developed to prepare in one step from said materials 17-oxo steroids, especially androst-4-ene-3,17-dione. From the latter compound it was possible to obtain 9-alpha-hydroxy-androst-4-ene-3,17-dione using a second microbiological step. This compound can be prepared even directly from the above-mentioned sterols, for example by using a specific *Mycobacterium fortuitum* strain, see British patent GB 1530730.

9-Alpha-hydroxyandrost-4-ene-3,17-dione is for several syntheses which lead to pharmacologically active steroids a suitable starting compound, because it is apt to functionalisation in the D-ring, as well as in the C-ring of the steroid nucleus. An important class of steroids containing many pharmacologically active compounds are the pregnanes. The corticosteroids, on the D-ring characterized by the (optionally esterified) 17-beta-hydroxyacetyl, 17-alpha-hydroxy substituents are particularly important representatives of this class. Many possess also a methyl or hydroxyl group on $C^{16}$. Multi-step chemical syntheses of pregnanes starting from the readily available above-mentioned 17-oxo steroids are well known in the art as illustrated by J. Org. Chem., Vol. 44, no. 9 (1979), 1582–1584 or by Bull. Chem. Soc. Jpn., Vol. 58, 981–986 (19,35) and by its references cited under 3) or by U.S. Pat. No. 4,500,461 and by its references cited in its introduction. In case the starting compound is a 9-alpha-hydroxy steroid, the first step is without exception a dehydration to a 9,11-dehydro steroid. The reason probably is that the presence of the tertiary 9-alpha-hydroxyl function is assumed to cause undesired rearrangements, especially in the steroid A-ring. See e.g. C. G. Bergstrom and R. M. Dodson, Chemistry and Industry, 1530 (1961) and L. J. Chinn & R. M. Dodson, J. Org. Chem. 24 (1959), 879. Because 9,11-dehydro steroids are believed to be more stable and a good starting point for the introduction of substituents on $C^9$ and $C^{11}$ the dehydration of 9-alpha-hydroxy steroids seemed to be an obvious reaction to begin every synthesis.

The object of the present invention is to provide new routes to tile above-said corticosteroids, which routes are characterized by the use of a common type of new intermediates, The invented intermediates belong to a novel class of 9-alpha-hydroxy steroids, characterised by a D-ring according to formula I

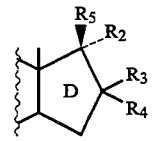

where
$R_2$ is —C≡CY (provided, when $R_4$ and Y both are hydrogen, $R_5$ is not acetyloxy), Y is hydrogen or halogen, optionally protected hydroxy, cyano, 1'-(1-6C)alkoxy-ethenyl, 1'-(1-6C) alkylthio-ethenyl, 1'-aryloxy-ethenyl, 1'-arylthioethenyl, 1',1'-trimethylenedithio-ethyl,
$R_3$ is hydrogen,
$R_4$ is hydrogen, hydroxy, alpha-methyl, beta-methyl or
$R_3$ and $R_4$ together form methylene, or
$R_2$ and $R_3$ together form a double bond,
$R_5$ is cyano, —COCHR$_1$R$_1'$, carbamoyl, hydroxy, ethynyl, haloethynyl, sulfonate, sulfite, trialkylsilyloxy, optionally halogenated (1–6C)carboxylic acyloxy, —C(=NR$_{80}$)—CH$_3$, —C(NHR$_{82}$)=CH$_2$, —C(=NR$_{80}$)—CH$_2$X, X is halogen,
$R_{80}$ is hydrogen, —(CO)—R$_{81}$, trialkylsilyl,
$R_{81}$ is hydrogen, (1–6C)alkyl, phenyl, phenyl substituted with 0–2 chlorine atoms, methyl or nitro groups,
$R_{82}$ is —(CO)—R$_{81}$, trialkylsilyl or
$R_2$ and $R_5$ together are carbonyl (provided $R_4$ is not H),
$R_1$ is halogen, optionally substituted benzoate or $R_1$ is (provided $R_4$ is not hydrogen), hydroxy, optionally halogenated (t-6C)carboxylic acyloxy, hydrogen,
$R_1'$ is hydrogen or halogen, halogen is chlorine, bromine or iodine.

More particularly the novel 9-alpha-hydroxy steroids are characterized by the general formula II

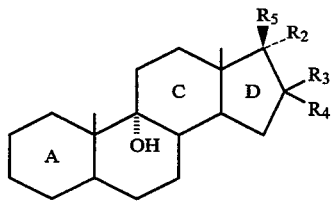

where $R_2$–$R_5$ are as defined above while the rings A, B, C and D may contain one or more double bonds, these double bonds being preferably present between $C^1$ and $C^2$, $C^3$ and $C^4$, $C^4$ and $C^5$, $C^5$ and $C^6$, $C^6$ and $C^7$, and/or $C^{11}$ and $C^{12}$, more preferably the double bond being present between $C^4$ and $C^5$ and when two or more double bonds are present especially the following systems are preferred $C^3$–$C^4$ and $C^5$–$C^6$, $C^4$–$C^5$ and $C^6$–$C^7$, and ($C^{19}$ absent) $C^1$–$C^2$, $C^3$–$C^4$ and $C^5$–$C^{10}$, while the rings A, B C and D in addition to the 9-alpha-hydroxyl group are optionally substituted by one or more hydroxyl groups, amino groups, oxygen atoms, halogen atoms or alkyl, alkylene, alkoxy or alkoxyalkoxy groups and are optionally disubstituted by one or more epoxy group, methylene groups, alkylenedioxy, alkylenedithio or alkyleneoxythio groups, and when the rings A, B, C and D are further substituted by a hydroxyl group besides the 9-alpha-hydroxyl group, suitable groups are 3-, 7-, 11-, 12- or 14-hydroxyl groups, when the rings A, B, C and D are substituted by an amino group, suitable amino groups are 3-alkylamino grips, preferably containing 1 through 4 carbon atoms, 3-dialkylamino groups wherein the alkyl groups are the same or different, each alkyl group preferably containing 1 through 4 carbon atoms, or amino groups in which the nitrogen atom together with the alkyl group form a heterocyclic ring, preferably containing 3 through 8 ring atoms, which ring optionally may contain an oxygen atom, particularly preferred are dimethylamino, diethylamino, pyrrolidino and morpholino substituents, when the rings A, B, C and D are substituted by an oxo group this group is preferably present at $C^3$, $C^{11}$ or $C^{12}$, when the rings A, B, C and D are substituted by a halogen atom, suitable halogen substituents are 6-or 11-fluorine, -chlorine or -bromine atoms, preferably 6-fluorine or -chlorine atoms, when the rings A, B, C, and D are substituted by an alkyl group, suitable alkyl groups are 1-, 2-, 6-, or 7-methyl groups, preferably 6-methyl, when the rings A, B, C and D are substituted by an alkoxy group, suitable alkoxy groups are 3-, 11- or 12-alkoxy groups containing 1 through 4 carbon atoms, preferably 3- or 11-methoxy or ethoxy groups, when the rings A, B, C and D are substituted by alkoxyalkoxy group, suitable groups are 3- or 11-methoxymethoxy, methoxyethoxy or tetrahydropyranyloxy groups, when the rings A, B, C and D are disubstituted, suitable substituents are an epoxy group at $C^1$ and $C^2$ or a methylene group attached to $C^1$ and $C^2$ or a 3,3-alkylenedioxy, a 3,3-alkylenedithio or a 3,3-alkyleneoxythio group, the alkylene group preferably containing 2 or 3 carbon atoms.

A particular group of the 9-alpha-hydroxy steroids of formula I are those of formula Ia

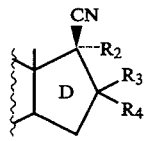

Ia in which $R_2$, $R_3$ and $R_4$ are as defined for the compounds of formula I. In this group of compounds $R_2$ preferably is optionally protected hydroxy and $R_4$ preferably is a methyl group.

Another group of interest of the 9-alpha-hydroxy steroids of formula I are those of formula Ib

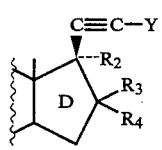

Ib in which $R_2$, $R_3$, $R_4$ and Y are as defined for the compounds of formula I. In this group of compounds $R_2$ preferably is optionally protected hydroxy, $R_4$ preferably is a methyl group and Y preferably is hydrogen.

A further particular group of the 9-alpha-hydroxy steroids of formula I are those of formula Ic

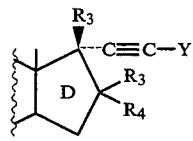

Ic in which $R_2$, $R_3$, $R_4$ and Y are as defined for the compounds of formula I. In this group of compounds $R_2$ preferably is optionally protected hydroxy, $R_4$ preferably is a methyl group ($R_2$ is not acetyloxy when $R_4$ and Y both are hydrogen) and Y preferably is hydrogen, chlorine or bromine.

Another group of interest of the 9-alpha-hydroxy steroids of formula I are those of formula Id

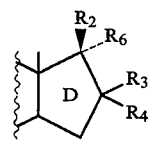

Id in which $R_3$ and $R_4$ are as defined for the compounds of formula I, $R_4$ preferably is a methyl group, $R_2$ is hydroxy, $R_6$ is acetyl, 1'-(1-6C)alkoxy-ethenyl, 1'-(1-6C)alkylthioethenyl, 1'-aryloxy-ethenyl, 1'-arylthio-ethenyl or 1',1'-trimethylenedithio-ethyl or when $R_6$ is acetyl, $R_2$ and $R_3$ together form a double bond.

A group of favourable 9-alpha-hydroxy steroids of formula I are those of formula Ie

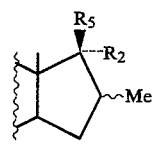

Ie where $R_5$ and $R_2$ are as defined for the compounds of formula I ∼ Me is alpha- or beta-methyl. Preferably $R_5$ is optionally protected hydroxy and $R_2$ is ethynyl, haloethynyl or $R_6$, where $R_6$ is as defined earlier, or $R_5$ is cyano, ethynyl, haloethynyl, acetyl, hydroxyacetyl or esterified hydroxyacetyl, where halo preferably is iodine and the ester preferably is an optionally halogenated (1–6C)carboxylic acyloxy group or an optionally substituted benzyloxy group and $R_2$ is optionally protected hydroxy.

Another group of preferred 9-alpha-hydroxy steroids are those of formula If

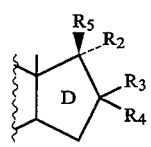

If in which $R_5$ is an optionally halogenated acetyl group, a hydroxyacetyl group or an esterified hydroxyacetyl group, where the ester group is as defined in the previous paragraph, $R_2$ and $R_3$ are as defined above and $R_4$ is hydroxy or methyl, preferably methyl.

A further group of preferred 9-alpha-hydroxy steroids are those of formula Ig

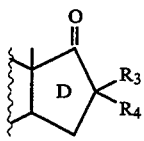

in which $R_3$ is hydrogen and $R_4$ is hydroxy, alpha-methyl or beta-methyl or $R_3$ and $R_4$ together form methylene.

From the foregoing it will be appreciated that the following compounds according to the invention are particularly preferred:

17 -beta-cyano-9-alpha,17-alpha-dihydroxy-16-R-androst-4-en-3-one, where R is hydrogen, hydroxy, alpha-methyl, beta-methyl or methylene, 17-alpha-cyano-9-alpha,17-beta-dihydroxy-16-R-androst-4-en-3-one, where R is hydrogen, hydroxy, alpha-methyl, beta-methyl or methylene, 17-alpha-ethynyl-9-alpha,17-beta-dihydroxy-16-R-androst-4-en-3-one, where R is hydrogen, hydroxy, alpha-methyl, beta-methyl or methylene, 17-alpha-haloethynyl -9-alpha,17-beta-dihydroxy-16-R-androst-4-en-3-one, where halo is chlorine or bromine an R is hydrogen, hydroxy, alpha-methyl, beta-methyl or methylene, 9-alpha-hydroxy-16-R-androst-4-en-3,17-dione, where R is hydroxy, alpha-methyl, beta-methyl or methylene, 17-alpha-acetyl-9-alpha,17-beta-dihydroxy-16-R-androst-4-en-3-one, where R is hydrogen, hydroxy, alpha-methyl, betamethyl or methylene, 17-alpha-(1'-ethoxyethenyl)-3-methoxy-16-R-androsta-3,5-diene-9-alpha, 17-beta-diol where R is hydrogen, hydroxy, alpha-methyl, beta-methyl or methylene.

A few 9-alpha-hydroxy compounds falling within the above definition of formula I have been obtained earlier by the non-chemical introduction of the 9-alpha-hydroxyl in steroids having no substituent on $C^9$, using Nocardia strains according to U.S. Pat. No. 4,397,947. These compounds are not used to be converted into other 9-alpha-hydroxy intermediates, but according to the earlier mentioned traditional chemistry they are meant to be dehydrated immediately to the corresponding 9,11-dehydro compounds. The relevant known 9-alpha-hydroxy steroids with a 17-beta-($-CO-CH_2^A$) substituent (where A is hydrogen, hydroxy or acetoxy) or with a 17-beta-acetoxy, 17-alpha-ethynyl substituent, always without $C^{16}$-substituents, are not comprised in the invention.

The use of the new 9-alpha-hydroxy steroids as intermediates in the synthesis of pharmacologically active pregnanes, especially corticosteroids provides several advantages, particularly:

1. In reactions involving 9-alpha-hydroxy steroids comprising the formation of an asymmetrical carbon atom, the desired enantiomer may be obtained selectively.

2. When dehydration is desired, for example as a first step in the functionalization of the $C^{11}$-atom, it is economical to combine the dehydration with one or more concomitant steps in the synthesis, e.g. the step of deprotection of protected functional groups using e.g. acid hydrolysis or the step of dehydration of a 17-alpha-hydroxy steroid resulting in a 16,17-dehydro steroid.

3. For some reactions the presence of a 9(11)-double bond is not desirable and the dehydration step better is postponed.

According to another aspect of the invention a chemical process is provided for the preparation of 9-alphahydroxy steroids. While the prior art only provides microbiological methods for the preparation of 9-alpha-hydroxy steroids, it has now surprisingly been found that these 9-alpha-hydroxy steroids can be prepared easily from other 9-alpha-hydroxy steroids using known steroid reactions, but which are supposedly agressive for steroids with a 9-alpha-hydroxyl group. Most reactions, however, can be carried out, necessitating only by exception particular precautions to spare the relevant hydroxyl group, since this group has appeared to be affected only in case reaction conditions are present which are either extreme, or which are chosen specifically to bring about a modification of the 9-alpha-hydroxyl group.

Therefore according to the invention it is possible to prepare 9-alpha-hydroxy-pregnanes and their 9-alphahydroxy intermediates starting from 9-alpha-hydroxyandrostanes.

An important group of steroids which are suited as starting compounds are the above-mentioned 17-keto steroids and especially the 17-keto steroids obtained by microbiological sterol degradation. The preferred starting compound is 9-alpha-hydroxy-androst-4-ene-3,17-dione. The compounds of the invention may be prepared by methods for analogous compounds well known in the art of steroid chemistry and described in e.g. Steroid Reactions, edited by Carl Djerassi (1962) or Fried and Edwards, Organic Reactions in Steroid Chemistry (1972).

Processes suited for the introduction of a 17-betaside chain or for the introduction of a substituent on $C^{16}$ are found in the survey literature e.g. Steroid Reactions and Organic Reactions in Steroid Chemistry (vide supra), Vol. 2, chapters 10 and 11, but also in specific patent literature, e.g. European patent applications 0153001 and 0189951, British patent application GB 2086907 and U.S. Pat. Nos. 4,342,702, 4,041,055 and 4,216,159.

The conditions which promote 9(11)-dehydration and which should be avoided are well known. For example heating for a prolonged time at extreme high or low pH values results in elimination of the hydroxyl group. With simple experiments it can be determined easily whether reaction conditions are detrimental to the maintenance of the 9-alpha-hydroxyl group. Spectrophotometrically ($^1$H NMR, $^{13}$C NMR, IR) or chromatographically (TLC, HPLC) the presence of the 9-alphahydroxyl group can be easily proved in the product.

The invention comprises the following types of reactions with 9-alpha-hydroxy steroids. They are presented by way of illustration and should not be conceived as a limitation of the invention:

A. Sensitive substituents, especially the 3-keto function, may be converted into protecting groups by known methods. For the $C^3$ ketone in 3-keto-4,5-dehydro steroids many protecting groups are available.

The keto group is preferably protected as enol ether, ketal or enamine by methods well known in the art. The preferred enol ether is the methyl or ethyl ether. The preferred ketal is the ethylene ketal; also the ethylenethio ketal has appeared to be useful. The preferred enamines are selected from the group consisting of pyrrolidine, morpholine and diethylamino amines. The enol ethers are prepared according to e.g. J. Org. Chem. 26, 3925 (1961), Steroid Reactions, supra 42–45, and U.S. Pat. No. 3,516,991. The ketals are prepared according to e.g. Steroid Reactions, supra, 3–35. The 3-enamines are prepared according to e.g:. U.S. Pat. No. 3,629,298 and Steroid Reactions, supra, 49–53.

For the protection of the hydroxyl group many protecting groups are available (see Steroid Reactions, supra, 67–82). The 17-hydroxyl group preferably is protected as ether or ester. Preferred ethers are the tetrahydropyranyl ether, alkoxyethyl ether or trialkylsilyl ether. Preferred esters are nitrate, alkylsulfonate, aryl sulfonate and optionally halogenated (1–6C)carboxylic acyl ester.

B1. The conversion of the 17-keto group into a 17-hydroxy, 17-cyano group, also called cyanohydrin group, provides a suitable start for the introduction of the $C^{17}$-carbon chain. The process is well elaborated and reagents are cheap and easily available. A suitable synthesis is provided by the so-called acetone cyanohydrin method. However, it is known from Bull. Chem. Soc. Jpn. 58, 978–980 (1985), that the application of this method on 17-keto androstanes without a 9-alpha-hydroxyl group results exclusively into the undesired 17-alpha-cyano, 17-beta-hydroxy epimer. Unexpectedly it has been found that said acetone cyanohydrin method when used with 9-alpha-hydroxyandrost-4-ene-3, 17-dione yields exclusively the desired 17-beta-cyano, 17-alpha-hydroxy epimer, while the 9-alpha-hydroxyl group remains unaffected. One may proceed e.g. as follows using one or more of the following steps.

1. reacting an optionally $C^3$-protected 9-alpha-hydroxy steroid with a D-ring according to formula

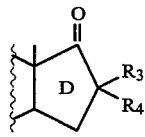

wherein $R_3$ is hydrogen, $R_4$ is hydrogen, hydroxy, alpha-methyl or beta-methyl, with potassium cyanide, acetone cyanohydrin or another cyanohydrin forming agent and 2. reacting the obtained 17-cyano, 17-hydroxy steroid with a 17-hydroxyl protecting agent to obtain the corresponding 17-cyano steroid with a protected 17-hydroxyl group, or, 2. reacting the obtained 17-cyano,17-hydroxy steroid with methane sulfonylchloride to obtain the corresponding 17-cyano, 17-methanesulfonyloxy steroid, 3. treating the product of the preceding step with a dehydrating agent resulting in the corresponding 17-cyano-16,17-dehydro steroid.

B2. When reacting a 9-alpha-hydroxy-17-keto steroid with trimethylsilyl cyanide, followed by acid hydrolysis according to W. J. Greenlee et al., Tetr. Lett., 24 (1983) 4554–4560 and P. G. Gassman et al., Tetr. 40 (1978) 3773–3776, the 17-alpha-cyano, 17-beta-hydroxy epimer still containing a 9-alpha-hydroxyl group is obtained. The corresponding beta-trimethylsilyloxy, 17-alpha-cyano compound may be isolated as an intermediate.

C. The conversion of the 17-keto group into a 17-ethynyl,17-hydroxyl group provides another suitable beginning for building a corticoid side chain. Methods For the transformation of the 17-keto function into a 17-ethynyl, 17-hydroxyl function are well known in the art. An extensive survey of this ethynylation reaction is found in the introduction of U.S. Pat. No. 4,618,456. For further synthesis to corticosteroids a 17-beta-ethynyl configuration is necessary. In case the product of the 17-ethynylation reaction shows the 17-alpha-ethynyl,17-beta-hydroxy configuration the compound should be epimerised to the desired configuration using one of the methods known in the art, see e.g. European patent applications EP 0053845 or EP 0063368, or H. Westmijze et al., Tetr. Lett. 21 (1980), 2665–2666; H. Hofmeister et al., Chem. Bet. 111 (1978) 3086–3093.

During the ethynylation as well as the subsequent epimerisation the 9-alpha-hydroxyl group appears to remain unaffected.

D. The introduction of a methyl group on the $C^{16}$-atom of 9-alpha-hydroxy steroids is an especially important process as a step in the preparation of a useful type of corticosteroids comprising betamethason and dexamethason. The reaction can be carried out either in one step or via the corresponding 16-methylene compound. In any case it is necessary to protect first properly the reactive 3-keto-4,5-dehydro group. The direct introduction of a 16-methyl substituent is described in e.g. European Patent Application EP 0115965, including its references to older methods. One may proceed e.g. as follows using one or more of the following steps.

1. reacting a $C^3$-protected 9-alpha-hydroxy steroid containing a D-ring according to formula

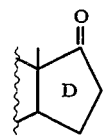

with a $C^{16}$-activating agent in the presence of an alkali metal alkoxide, 2. reacting the product of step 1 with a methylating agent, 3. reacting the product of step 2 with a strong base in a solvent containing an alcohol, to give the corresponding 9-alpha-hydroxy steroid containing a D-ring according to formula

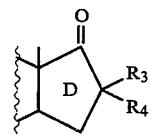

where $R_3$ is hydrogen, $R_4$ is beta-methyl.

The introduction of a 16-methylene function is teached by G. Schneider et al., Synthesis 1983, 665–669 and in U.S. Pat. No. 4,416,821. A way to reduce the methylene group to a methyl group is found in U.S. Pat. Nos. 3,130,209, and 3,115,508 yielding compounds with respectively a 16-alphamethyl or a 16-beta-methyl substituent. One may proceed e.g. as follows using one or more of the following steps.

1. reacting a $C^3$-protected 9-alpha-hydroxy steroid containing a D-ring according to formula with a C16-activating agent in the presence of an alkali metal alkoxide, 2. reacting the product of step 1 with formaldehyde or a formaldehyde generating agent, to give the corresponding 9-alpha-hydroxy steroid containing a D-ring according to formula

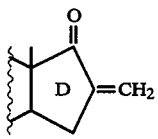

3. reacting the product of step 2, with a reducing agent to give the corresponding 9-alpha-hydroxy steroid containing a D-ring according to formula

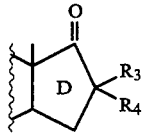

where $R_3$ is hydrogen, $R_4$ is alpha-methyl or beta-methyl.

In spite of rather severe reaction conditions the 9-alpha-hydroxyl group appears to remain present in the product. The obtained 9-alpha-hydroxy-16-methyl or 9-alpha-hydroxy-16-methylene compound can be converted further into the corresponding 17-beta-cyano, 17-alpha-hydroxy compound or into the corresponding 17-ethynyl,17-hydroxy compound according to the methods mentioned before.

E. For the preparation of 17-acetyl steroids starting from 17-oxo-steroids a special type of compounds may be used which are known as masked acetyl reagents. These compounds, belonging to the group of masked acyl reagents, are characterized in that the reactivity of the carbonyl carbon is changed by the masked carbonyl group. The principles and applications of this "umpolung" concept are reviewed by D. Seebach, Chemistry and Industry (1974) 687–692 and by B. T. Gröbel and D. Seebach, Synthesis (1977) 357–367. In the presence of strong bases masked acyl reagents form stable anions which easily react with the carbonyl carbon and form an intermediate which is easily hydrolysed into an acetyl group, affording a 17-acetyl steroid, when reacted with a 17-oxo-steroid. Masked acyl reagents are extensively discussed further in Tetrahedron vol. 32, 1943–1971 and in European patent application EP 0189951, in which they are used for the introduction of the pregnane side chain.

Preferred representatives of said class are alkyl or aryl vinyl ethers, alkyl or aryl vinyl thioethers or 1,1-trimethylenedithio)ethane.

The use of alkyl vinyl ethers is illustrated by Baldwin et al., J. Am. Chem. Soc. 96 (1974) 7125 or J. Org. Chem. 41 (1976) 2312.

The use of the above preferred group of masked acy reagents according to the invention results in 9-alphahydroxy steroids characterized by a D-ring according to the formula

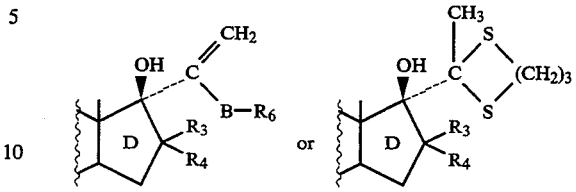

where B is oxygen or sulfur, $R_6$ is (1–6C)alkyl or aryl, whereafter a treatment with an acid yields the corresponding 17-alpha-acetyl, 17-beta-hydroxy steroid.

To obtain the desired beta-acetyl epimer the compound may be dehydrated to the corresponding 16,17-dehydro steroid, epoxidised and hydrogenated (Organic Reactions in Steroid Chemistry, supra, vol. 2, 195–197). A special epimerisation process is described for the corresponding 16-methylene compound in European Patent Application EP 0104054.

F. According to Fried and Edwards, Organic Reactions in Steroid Chemistry, supra, Vol. 2, 132–136, 9-alpha-hydroxy steroids with a protected 3-keto-function, a protected 17-alpha-hydroxyl group and a 17-beta-cyano group may be converted into the corresponding 17-beta-(1-iminoethyl) compounds which, without isolation, are further converted into the corresponding 17-beta-acetyl compounds:

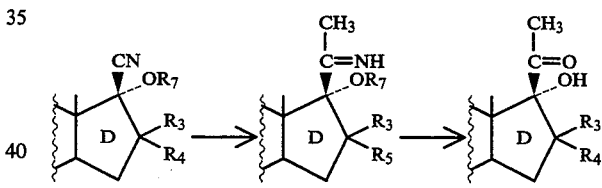

$R_7$ is a protecting group, preferably a tetrahydropyranyl or an alkoxy ethyl group. The imino group may be substituted by a (1–6C)carboxylic acyl group or a trialkyl silyl group by treating the compound with an acylating or silylating agent (see e.g. EP 0153001). For a general survey of reactions on $C^{21}$ see Organic Reactions in Steroid Chemistry, supra, vol. 2, 162–227. To obtain compounds with a corticoid side chain the $C^{21}$-methyl group is first substituted with halogen and subsequently halogen is substituted by an ester group, which finally may be hydrolised. Halogen may be chlorine or bromine, but preferably is iodine. The ester group may be a (1–6C)carboxylic acyloxy group, optionally substituted with 1–3 halogen atoms or a benzoyloxy group with a phenyl group which is optionally substituted with 0–2 chlorine atoms, methyl or nitro groups. Specific examples are described by M. Numazama et al. , J. Org. Chem. 50 (1985) , 81–84; O. Halpern et al., J. Am. Chem. Soc. 81 (1959), 439 and E. S. Rothman et al., J. Org. Chem. 25 (1960), 1966. One may proceed e.g. as follows using one or more of the following steps.

1. treating a 9-alpha-hydroxy steroid containing a D-ring according to formula

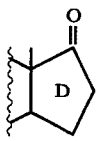

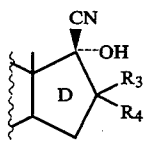

where $R_3$ is hydrogen, $R_4$ is hydrogen, hydroxy, alpha-methyl or beta-methyl with a $C^3$-protecting agent, followed or preceded by 2. converting the 17-alpha-hydroxyl group into a protected hydroxyl group, 3. treating the resulting compound with a methylating agent, to obtain the corresponding 17-beta-1'-iminoethyl steroid, 4. treating the obtained imino compound with an acylating or silylating agent, to obtain the corresponding N-iminoacyl or N-iminosilyl compound, 5. reacting the compound resulting from step 3 or step 4 with a $C^{21}$-halogenating agent, followed or preceded by deprotection of protected groups on $C^3$, $C^{17}$ and/or $C^{20}$, 6. introducing an optionally halogenated (1-6C)carboxylic acyloxy group or an optionally substituted benzoyloxy group on $C^{21}$, 7. hydrolysing the product of the preceding step to obtain the corresponding 21-hydroxypregnane, 8. dehydrating the product according to any one of the preceding steps resulting in the corresponding 16,17-dehydro steroid.

G. 9-Alpha-hydroxy steroids with a 17-ethynyl-17-hydroxy substitution may be further processed to the corresponding (optionally esterified) 17-beta-acetyl, 17-alpha-hydroxy or 17-beta-hydroxyacetyl, 17-alpha-hydroxy compounds by methods well known in the art (see e.g. I. Nitta et al., Bull. Chem. Soc. Jpn. 58, (1985), 981–986; C. Burgess et al. , J. Chem. Soc. (1962) , 4995–5004; European Patent Application 0123241; Hofmeister et al., Liebigs Ann. Chem., 423–426 (1987)), Organic Reactions in Steroid Chemistry, supra, Vol. 2, 203–227. In case the starting compound is characterized by a 17-beta-ethynyl substituent the aimed compounds may be prepared according to the following steps:

1. treating a 9-alpha-hydroxy steroid containing a D-ring according to formula

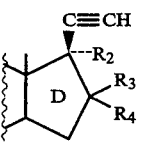

where $R_2$ is esterified hydroxy, $R_3$ is hydrogen, $R_4$ is hydrogen, hydroxy, alpha-methyl or beta-methyl, or $R_3$ and $R_4$ together are methylene with a hydrating agent in the presence of a halogenating agent to obtain the corresponding 21,21-dihalo-20-keto pregnane, where halo may be chlorine, bromine and preferably is iodine, 2. introducing an optionally halogenated (1-6C)carboxylic acyloxy group or an optionally substituted benzoyloxy group on $C^{21}$, 3. hydrolysing the ester group on $C^{21}$, 4. dehydrating the product according to any one of the preceding steps resulting in the corresponding 16,17-dehydro steroid, where the ester groups mentioned in step 2 are as defined in the preceding paragraph F or according to the steps:

1. treating a 9-alpha-hydroxy steroid containing a D-ring according to formula

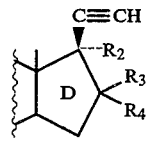

where $R_2$ is hydroxy, $R_3$ is hydrogen, $R_4$ is hydrogen, hydroxy, alpha-methyl or beta-methyl, or $R_3$ and $R_4$ together are methylene, with a hydrating agent to obtain the corresponding 17-betaacetyl steroid, 2. dehydrating the obtained product resulting in the corresponding 16,17-dehydro steroid.

In case the starting compound is characterized by a 17-alphaethynyl or a 17-alpha-haloethynyl substituent the aimed compounds may be obtained according to the steps 1. treating a 9-alpha-hydroxy steroid containing a D-ring according to formula

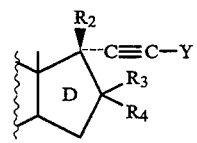

where Y is a hydrogen, chlorine or bromine atom, $R_2$ is optionally halogenated (1-6C)carboxylic acyloxy, $R_3$ is hydrogen, $R_4$ is hydrogen, hydroxy, alpha-methyl, beta-methyl or $R_3$ and $R_4$ together are methylene, with an agent causing epimerisation of the $C^{17}$-substituents and, in case Y is hydrogen, hydrating the ethynyl group to a 17-beta-acetyl group or, in case Y is halogen, hydrating the haloethynyl group to a 17-beta-haloacetyl group 2. substituting $C^{21}$-halogen with an optionally halogenated (1-6C)carboxylic acyloxy group or an optionally substituted benzoyloxy group, 3. deprotecting possible protected groups on $C^3$ and/or $C^{17}$, 4. hydrolysing the ester group on $C^{21}$ 5. dehydrating the product according to any one of the preceding steps resulting in the corresponding 16,17-dehydro steroid, where the ester groups mentioned in step 2 are as defined in the preceding paragraph F. The epimerisation reaction of step 1 is already discussed in paragraph C.

The 9-alpha-hydroxy steroids of the invention or prepared according to the invention may be dehydrated methods known in the art. The corresponding 9,11-dehydro steroid may be obtained e.g. according to German patent application DE 2814747 using sulfuric acid treatment or as described in U.S. Pat. No. 4,102,907 via a 9-alpha-sulfinate ester. The not yet published European patent application 87201114.3 teaches a method using silica gel and p-toluene sulfonic acid.

Dehydration of a 17-alpha-hydroxy steroid into the corresponding 16,17-dehydro compound may be carried out for example with a mixture of phosphorus oxychloride and pyridine. Alternatively the 17-alpha-hydroxyl group may be esterified first with methylsulfonic acid and treated next with collidine to obtain the 16(17) double bond with in both cases preservation of the 9-alpha-hydroxyl group. The conditions for dehydration may be chosen in such a way, that the 17-alpha-hydroxyl group and the 9-alpha-hydroxyl group are eliminated in the same reaction.

Another advantageous combination of reactions is when the dehydration reaction to a 9,11-dehydro steroid takes place concomitantly with another step of the synthesis e.g. the deprotection of protected substituents on $C^3$ and $C^7$. For example a treatment with sulfuric acid of a 9-alpha-hydroxy steroid bearing a 3,3-ethylenedioxy and a 17-alphatetrahydropyranyloxy substituent yields in one step a 17-alpha-hydroxy-3-oxo-9,11-dehydro steroid. The 9,11-dehydrated products are usually known compounds and provide suitable starting compounds for introducing pharmacologically interesting substituents, for example the 11-hydroxyl group and/or a 9-halogen atom.

9(11)-Dehydration of the 9-alpha-hydroxy compounds prepared according to the invention also may be used to confirm the structure of these compounds by comparing the physical data of the obtained products, if known, with those of reference compounds.

Compounds according to the invention or prepared according to the invention are suitable intermediates for the preparation of pharmacologically active pregnanes, particularly corticosteroids, but they also have glucocorticoid or progestational activity of their own. Hence the invention relates also to pharmaceutical preparations having as an active ingredient a therapeutical amount of asteroid according to this invention.

The invention is illustrated by the following examples. For all preparations the presence of the 9-alphahydroxyl group has been confirmed by $C^{13}$ NMR. NMR-spectra are recorded with 360 MHz proton NMR and with 90 MHz $C^{13}$ NMR. The NMR data are recorded in $\delta$ (ppm) units downfield from TMS. All percentages are by weight unless otherwise stated.

EXAMPLE 1

9-Alpha-hydroxy-3-methoxyandrosta-3,5-dien-17-one

To a stirred suspension of 2.2 g of 9-alphahydroxy-androst-4-ene-3,17-dione in 30 ml of methanol 2.2 ml of trimethyl orthoformate were added, followed by a dropwise addition of a 5% solution of sulfuric acid in methanol until a pH-meter showed a value of 0.4. After stirring for 1 hour at room temperature triethylamine was added until a pH is 7. Then 2 ml of water were added and the pH adjusted to 2.5 by the addition of 1N sulfuric acid and the mixture stirred at room temperature for another 30 minutes to hydrolyse formed 17-ketal. Afterwards the pH was adjusted to 9 with triethylamine, 20 ml of water were added and the mixture stirred for 30 minutes while cooling in an ice bath. The precipitate was filtered, washed with cold water and dried. The yield was 1.3 g of 9-alpha-hydroxy-3-methoxyandrosta-3,5-dien-17-one.

NMR (CDCl$_3$): 0.905 (C$^{18}$H$_3$), 1.119 (C$^{19}$H$_3$), 3.57 (OCH$_3$), 5.17 (C$^4$H), 5.31 (C$^6$H).

IR (KBr): 3580 (OH), 1734 (CO), 1645 (C=C), 1612 (C=C).

EXAMPLE 2

The experiment of the previous example was repeated under the same conditions, except that 33 g starting compound were suspended in 150 ml methanol; yield 27.7 g.

EXAMPLE 3

9-Alpha-hydroxy-3-methoxy-16-methylene-androsta-3,5-dien-17-one

A stirred solution of 0.5 g of 9-alpha-hydroxy-3-methoxyandrosta-3,5-dien-17-one and 0.36 ml of diethyl oxalate in 5.5 ml of dry tetrahydrofuran was flushed with nitrogen and cooled to 5° C. Under nitrogen 0.46 ml of a 25% w/v solution of sodium methanolate in methanol were added dropwise..After the addition stirring was continued for 1 hour at 5° C. and then for 20 minutes at room temperature. Next the reaction mixture was again cooled to 5° C. and 0.025 ml of acetic acid, 0.17 ml of triethylamine, 0.7 ml of methanol and 0.07 ml of formalin were successively added. After 40 minutes of stirring at 5° C. the cooling bath was removed and another 0.14 ml of formalin were added. The stirring was continued for 45 minutes, 2.5 ml of water were added and the mixture extracted with 2.5 ml of ethyl acetate. The organic extract was washed with water, dried on anhydrous sodium sulphate and then evaporated to dryness. The residue was treated with methanol, the crystalline product filtered and dried. The yield was 100 mg of 9-alpha-hydroxy-3-methoxy-16-methyleneandrosta-3,5-dien-17-one.

NMR (CDCl$_3$): 0.854 (C$^{18}$H$_3$), 1.051 (C$^{19}$H$_3$), 3.51 (OCH$_3$) 5.10, (C$^4$H), 5.24 (C$^6$H), 5.31 and 6.00 (CH$_2$). IR (KBr): 3575 (OH), 1740 (C=O), 1651, 1642, 1626 (C=C); m.p.: 148°–153° C.

The experiment was repeated under the same conditions except that the reaction mixture was stirred for 2 hours at room temperature. Starting from 50 g of 9-alphahydroxy-3-methoxyandrosta-3,5-dien-17-one 31.0 g of the title compound was obtained.

EXAMPLE 4

9-Alpha-hydroxy-16-methylene-androst-4-ene-3,17-dione

A solution of 2.5 g of 9-alpha-hydroxy-3-methoxyandrosta-3,5-dien-17-one and 1.8 ml of diethyl oxalate in 27.5 ml of anhydrous tetrahydrofuran was stirred under nitrogen and cooled to 5° C. Then 2.3 ml of a 25% w/v solution of sodium methanolate in methanol were added dropwise in 2 minutes. After the addition the reaction mixture was stirred for 5 minutes at 5° C. and then for 1 hour at room temperature. A thin layer chromatography (SiO$_2$, toluene/acetone 9/1) indicated that after 1 hour the transformation was complete. The mixture was again cooled to 5° C. and 0.12 ml of acetic acid, 0.87 ml of triethylamine, 3.5 ml of methanol and 0.35 ml of formalin were added successively. Stirring was continued for 1 hour at 5° C., another 0.7 ml of formalin were added and the mixtured stirred for 45 minutes at room temperature. Then 10 ml of ethyl acetate and 10 ml of water were added, the pH adjusted to 0.5 and stirring continued for 2.5 hours. Then the organic layer was separated and evaporated to dryness. The residue was solved in methylene chloride, dried over anhydrous sodium sulphate and the solvent evaporated. The residue was triturated with methanol and the crystalline solid filtered, washed with cold methanol and dried. The yield was 1.71 g of 9-alpha-hydroxy-16-methylene-androst-4-ene-3,17-dione.

NMR (CDCl$_3$): 0.866 (C$^{18}$H$_3$), 1.269 (C$^{19}$H$_3$), 3.01 (OH), 5.32 and 5.97 (CH$_2$), 5.76 (C$^4$H).

IR (KBr): 3460 (OH), 1760 (CO), 1650 (CO), 1620 (C=C); m.p. 245°–250° C. (dec.).

EXAMPLE 5

9-Alpha-hydroxy-3-methoxy-16-beta-methylandrosta-3,5-dien-17-one

A 25% w/v solution of sodium methoxide in methanol (0.92 ml) was added at 5° C. to a solution of 9-alphahydroxy-3-methoxyandrosta-3,5-dien-17-one (1 g) and diethyl oxalate (0.72 ml) in tetrahydrofuran (10 ml). After stirring for 1 hour at room temperature sodium bicarbonate (110 mg) was added. After evaporation of the solvent acetone (6 ml) and methyl iodide (1 ml) were added. The reaction mixture was heated during 18 hours at 65° C. in a sealed flask. After cooling to room temperature a solution of methyl bromide (3.5 ml) in acetone was added. The reaction mixture was stirred for 15 minutes and evaporated at reduced pressure to dryness, after which methanol (10 ml) and a 25% w/v solution of sodium methoxide in methanol (0.7 ml) were added at $-10°$ C. After stirring for 15 minutes water (10 ml) and acetic acid were added. The reaction mixture was extracted twice with methylene chloride (with 1% v/v triethylamine). The organic layers were combined, dried and evaporated. The crude product was purified over silica gel (toluene with 1% triethylamine) to afford 100 mg 9-alphahydroxy-3-methoxy-16-beta-methylandrosta-3,5-dien-17-one.

IR (KBr): 3460 (OH), 1715 (CO), 1630, 1660 (C=C).
NMR (CDCl$_3$):=0.864 (C$^{18}$H$_3$), 1.115 (C$^{19}$H$_3$), 1.21 (C$^{16}$H$_3$), 3.57 (OCH$_3$), 5.18 (C$^4$H), 5.33 (C$^6$H).

EXAMPLE 6

9-Alpha-hydroxy-3-methoxy-16-beta-methylandrosta-3,5-dien-17-one

A suspension of 10% palladium on carbon (200 mg) in tetrahydrofuran (10 ml) was washed with nitrogen and saturated with hydrogen. A solution of 9-alpha-hydroxy-3-methoxy-16-methylene-androsta-3,5-dien-17-one (0.5 g) in tetrahydrofuran (10 ml) which was also washed with nitrogen and saturated with hydrogen was added in 5 minutes. The reaction mixture was stirred for 1 hour under a hydrogen atmosphere and washed with nitrogen. After filtration over filter aid (Dicalite) 2 drops of triethylamine were added to the filtrate, which was then evaporated under reduced pressure to give an oil which crystallized in methanol (5 ml). After cooling at 5° C. for 1 hour the precipitate was filtered, washed with cold methanol and dried. Yield: 130 mg of 9-alpha-hydroxy-3-methoxy-16-beta-methylandrosta-3,5-dien-17-one. IR- and NMR-spectra were identical with the spectra of the product obtained according to Example 5.

EXAMPLE 7

9-Alpha-hydroxy-16-beta-methylandrost-4-ene-3,17-dione

A suspension of 10% palladium on carbon (2.4 g) in tetrahydrofuran (100 ml) was washed with nitrogen and saturated with hydrogen. A solution of 9-alpha-hydroxy-3-methoxy-16-methylene-androsta-3,5-dien-17-one (12 g) in tetrahydrofuran, which was also washed with nitrogen and saturated with hydrogen, was added in 5 minutes. The reaction mixture was stirred for 1 hour under a hydrogen atmosphere and washed with nitrogen. After adding some filter aid (Dicalite) the reaction mixture was stirred and filtered. The filtrate was concentrated under reduced pressure to give an oil (14 g), after which methanol (100 ml) and water (2,5 ml) were added. The reaction mixture was stirred for 15 minutes at pit 0.8. After adding water (10 ml) the precipitate was filtered and washed with methanol/water. The crude product was crystallized from methylene chloride to afford 6.1 g of 9-alpha-hydroxy-16-beta-methylandrost-4-ene-3,17-dione.

IR (KBr): 3465 (OH), 1735 (CO), 1650 (CO), 1605 (C=C).
NMR (CDCl$_3$+DMSO-d6): 0.876 (C$^{18}$H$_3$), 1.21 (C$^{16}$H$_3$), 1.336 (C$^{19}$H$_3$), 5.84 (C$^4$H).

EXAMPLE 8

17-Beta-cyano-9-alpha, 17-alpha-dihydroxyandrost-4-en-3-one

A suspension of 250 mg of 9-alpha-hydroxyandrost-4-ene-3,17-dione and 250 mg of potassium cyanide in 2 ml of methanol was stirred at room temperature. To this mixture 85 microliter of acetic acid were added and the stirring continued for 17 hours at room temperature. Then 150 microliter of acetic acid and 8.75 ml of water were added. The crystalline precipitate was collected by filtration, washed with water and dried. The crude product was crystallized from ethanol containing 1% v/v acetic acid. The yield was 170 mg of pure 17-beta-cyano-9-alpha,17-alpha, dihydroxyandrost-4-en-3-one.

M.p. 209–213; $[\alpha]_D^{23} = +99.0°$ (c=0.3; dioxane).
IR (KBr): 3410 (OH), 2220 (CN) and 1625 (CO).
NMR (DMSO-d6): 0.859 (C$^{18}$H$_3$), 1.252 (C$^{19}$H$_3$), 4.16 (OH), 5.65 (C$^4$H), 6.22 (OH).

EXAMPLE 9

17-Beta-cyano-9-alpha, -17-alpha-dihydroxyandrost-4-en-3-one

A mixture of 250 mg of 9-alpha-hydroxyandrost-4-ene-3,17-dione, 375 microliters of acetone cyanohydrin and 5 microliters of 50% aqueous sodium hydroxide solution was heated on a steam bath until a clear solution was obtained and then cooled to room temperature. After standing for one night at room temperature during which time product crystallized, the reaction mixture was neutralised with one drop of acetic acid, acetone was added and the mixture stirred. The crystals were filtered, washed with acetone and dried. The product was recrystallized from ethanol containing 1% v/v acetic acid yielding 99 mg of pure 17-beta-cyano-9-alpha, 17-alpha-dihydroxyandrost-4-en-3-one; M.p. 209°–211° C., $[\alpha]_D^{25} = +98.4°$ (c=0.5; dioxane). The IR and NMR spectra were identical with those of the product described under Example 8.

EXAMPLE 10

17-Beta-cyano-9-alpha, 17-alpha-dihydroxy-16-beta-methylandrost-4-en-3-one

A suspension of 1.0 g of 9-alpha-hydroxy-16-betamethylandrost-4-ene-3,17-dione and 5 g of potassium cyanide in 4 ml of methylene chloride and 4 ml of methanol was stirred at room temperature. After the addition of 1.7 ml of acetic acid stirring was continued for 6 days at room temperature. After the addition of 3 ml of acetic acid the reaction mixture was evaporated under reduced pressure to dryness. The residue was stirred with water, filtered, washed with water and dried. The crude product (0.82 g) was purified over silica gel with toluene/acetone 5/1. Crystallization from ethanol afforded 299 mg of pure 17-cyano-9-alpha, 17-dihydroxy-16-beta-methyl-androst-4-en-3-one.

M.p. 248°–251° C.; $[\alpha]_D^{21} + 102°$ (c=0.5; dioxane).

IR (KBr): 3418 (OH), 2221 (CN), 1630 (CO).

NMR (CDCl$_3$+DMSO-d6): 0.949 (C$^{18}$H$_3$), 1.29 (C$^{16}$H$_3$), 1.310 (C$^{19}$H$_3$), 3.26 (OH), 5.76 (OH), 5.80 (C$^4$H).

EXAMPLE 11

17-Beta-cyano-17-alpha-hydroxyandrosta-4,9(11)-dien-3-one 443 mg of 17-beta-cyano-9-alpha, 17-alphadihydroxyandrost-4-en-3-one were stirred in 1.1 ml of 70% sulfuric acid. After 16 hours water was added, the precipitate filtered, washed with water and dried. The crude product (376 mg) was crystallized from methanol. 206 mg of a mixture of two products was obtained. Chromatography (SiO$_2$; elution with toluene+5% acetone) yielded 65 mg of pure 17-beta-cyano-17-alpha-hydroxyandrosta-4,9 (11)-dien-3-one; M.p. 199°–201° C.; $[\delta]_D^{25} = 98.0°$ (c=0.5; dioxane).

IR (KBr): 3225 (OH), 2220 (CN), 1650 (CO) and 1614 (C=C).

NMR (CDCl$_3$+DMSO-d6): 0.915 (C$^{18}$H$_3$), 1.357 (C$^{19}$H$_3$), 5.58 (C$^{11}$H), 5.67 (OH) and 5.74 (C$^4$H).

These values agree with the data of Nitta et al. in Bull. Chem. Soc. Jpn. 58, 978–980 (1985) for 17-beta-cyano-17-alpha-hydroxyandrosta-4,9(11)-dien-3-one.

Of the second, more polar product 37 mg was obtained. It appeared to be 17-beta-carbamoyl,17-alphahydroxyandrosta-4,9 (11)-dien-3-one.

IR (KBr): 3460 (OH), 3283 (NH), 3038 (=CH), 1665 (2×CO) 1620 (C=C), 1589 (C=C).

NMR (CDCl$_3$+DMSO-d6): 0.685 (C$^{18}$H$_3$), 1.352 (C$^{19}$H$_3$), 4.93 (OH), 5.45 (C$^{11}$H), 5.68 (C$^4$H), 6.56, 6.76 (2×br, s,NH$_2$).

EXAMPLE 12

7-Cyano-9-alpha-hydroxyandrosta-4,16-dien-3-one

Under a nitrogen atmosphere 2.5 ml of methylsulfonylchloride were added to a stirred suspension of 1 g of 17-beta-cyano-9-alpha, 17-alpha-dihydroxyandrost-4-en-3-one in 5 ml of pyridine. After stirring for 8 hours at room temperature the reaction mixture was poured dropwise into a mixture of 100 g of ice and 100 ml of 1N aqueous hydrochloric acid. After extraction with isobutyl methyl ketone the organic layer was washed with water, and evaporated under reduced pressure to afford 17-beta-cyano-9-alpha-hydroxy-17-alphamethylsulfonyloxyandrost-4-en-3-one, which without further purification was boiled in 10 ml of collidine under nitrogen for one hour. The solution was cooled to room temperature, after which 25 ml of water, 75 ml of isobutyl methyl ketone and 10 ml of 37% aqueous hydrochlorid acid were added. After extraction the isobutyl methyl ketone layer was washed three times with water and evaporated under reduced pressure till dryness. The crude product was purified by chromatography (silica gel; toluene/acetone 19/1). Crystallization from ethyl acetate afforded 469 mg of 17-cyano-9-alphahydroxyandrosta-4,16-dien-3-one.

IR (KBr): 3438 (OH), 2201 (CN), 1662 (CO), 1638 (C=C), 1584 (C=C).

NMR (CDCl$_3$): 0.982 (C$^{18}$H$_3$), 1.352 (C$^{19}$H$_3$), 2.41 (OH), 5.86 (C$^4$H), 6.65 (C$^{16}$H).

The intermediate compound 17-beta-cyano-9-alphahydroxy-17-alpha-methylsulfonyloxyandrost-4-en-3-one has been isolated and identified by NMR (CDCl$_3$): 1.071 (C$^{18}$H$_3$), 1.337 (C$^{19}$H$_3$), 2.41 (OH), 3.18 (SO$_2$CH$_3$), 5.87 (C$^4$H).

EXAMPLE 13

The same product as in the previous example was obtained by refluxing a suspension of 0.5 g of 17-beta-cyano-9-alpha, 17-alpha-dihydroxyandrost-4-en-3-one in a mixture of 2.5 ml of phosphorus oxychloride and 5 ml of pyridine for 10 minutes. After cooling the mixture was dropped into a mixture of 100 g of ice, 100 ml of water and 5 ml of 37% aqueous hydrochlorid acid. The crystals were filtered, washed with water and dried. Yield 0.20 g.

EXAMPLE 14

17-Cyanoandrosta-4,9 (11), 16-trien-3-one

A solution of 150 mg of 17-cyano-9-alphahydroxyandrosta-4,16-dien-3-one in 375 microliter of sulfuric acid was stirred for 5 hours at room temperature. After addition of 5 ml of water the precipitate was filtered, washed with water and dried. This crude product (130 mg) was purified by chromatography (silica gel, elution with toluene+2% v/v acetone). Crystallization from hexane afforded 67 mg of pure 17-cyanoandrosta-4,9(11),16-trien-3-one.

M.p. 148.5°–149.5° C.

IR (KBr): 3062, 3038, 3015 (=CH), 2203 (CN), 1666 (CO), 1629, 1611, 1591 (C=C).

NMR (CDCl$_3$): 0.915 (C$^{18}$H$_3$), 1.369 (C$^{19}$H$_3$), 5.57 (C$^{11}$H), 5.76 (C$^4$H), 6.66 (C$^{16}$H).

EXAMPLE 15

17-Alpha-ethynyl-9-alpha, 17-beta-dihydroxy-androst-4-en-3-one

A solution of 9-alpha-hydroxy-3-methoxyandrosta-3,5-dien-17-one (1.072 g) and lithium acetylide.ethylenediamine complex (90%) (1.663 g) in dry tetrahydrofuran (7 ml) is stirred at room temperature for 20 hours. The reaction contents are then cooled and brought to pH 1.0 with 4N HCl and stirred at room temperature for 45 min. Thereafter, most of the tetrahydrofuran is evaporated under reduced pressure and the contents extracted with chloroform. The combined chloroform extracts are washed with saline and dried over anhydrous magnesium sulfate. The solvent is removed under reduced pressure and the product dried under vacuum. Yield is 0.708 g. This product has been further purified by chromatography, using toluene:acetone=2:1 as the eluent to give the title compound.

IR (KBr): 3616 (OH), 3400 (OH), 3266 (=CH), 2094 (C=C), 1646 (CO), 1607 (C=C).

NMR (DMSO-d$_6$): 0.748(C$^{18}$H$_3$), 1.230(C$^{19}$H$_3$), 3.27(C$^{21}$H), 4.03(OH), 5.23(OH), 5.62(C$^4$H).

$^{13}$C-NMR (DMSO-d$_6$): 12.03(C$^{18}$), 19.56(C$^{19}$), 75.36(C$^{21}$), 125.01(C$^4$), 75.04(C$^9$), 78.06(C$^{17}$), 89.15(C$^{20}$), 171.03(C$^5$).

Mass spectrum m/e: 328, 310, 295, 284.

EXAMPLE 16

17-Alpha-ethynyl-9-alpha-hydroxy-17-beta-nitrooxyandrost-4-en-3-one

To a stirred suspension of 17-alpha-ethynyl-9-alpha, 17-beta-dihydroxyandrost-4-en-3-one (411 mg) in acetic anhydride (3.1 ml) fuming nitric acid (0.31 ml) was added dropwise at −25° C. under nitrogen. After stirring for 1 hour at −20° C. the reaction mixture was poured into 25 ml of ice water and stirred. The resulting precipitate was filtered and dissolved in methylene chloride. This solution was washed with water until neutral, dried and evaporated under reduced pressure to afford the title compound (0,44 g, yield 94%)

NMR (CDCl$_3$/DMSO-d$_6$ 3/1): 0,963 (C$^{18}$H$_3$), 1.310 (C$^{19}$H$_3$), 3.08 (C$^{21}$H), 3.69 (OH), 5.75 (C$^4$H).

IR (KBr): 3391, 3315, 2143, 1650, 1628, 1308, 1289.

EXAMPLE 17

17-Beta-ethynyl-9-alpha, 17-alpha-dihydroxyandrost-4-en-3-one

To a solution of 17-alpha-ethynyl-9-alpha-hydroxy-17-beta-nitrooxyandrost-4-en-3-one (400 mg) in tetrahydrofuran (1.2 ml), water (1.2 ml) and silver nitrate (46 mg) were added. The reaction mixture was stirred for 72 hours at room temperature, after which the tetrahydrofuran was evaporated under reduced pressure. Nitric acid (65% 0.6 ml) was added, and the mixture was extracted with methylene chloride, washed with water until neutral and evaporated under reduced pressure to give the crude title compound (0.34 g). The crude product was crystallized from tetrahydrofuran and hexane.

NMR (CDCl$_3$): 0.923(C$^{18}$H$_3$), 1.335(C$^{19}$H$_3$), 2.51(C$^{21}$H), 5.88(C$^4$H).

NMR (DMSO-d$_6$): 0.790(C$^{18}$H$_3$), 1.233(C$^{19}$H$_3$), 3.19(C$^{21}$H), 4.02(OH), 5.07(OH), 5.62(C$^4$H).

EXAMPLE 18

9-Alpha,17-alpha-dihydroxypregn-4-ene-3,20-dione

17-Beta-ethynyl -9-alpha,17-alpha-dihydroxyandrost-4-en-3-one (80 mg) was suspended in a mixture of acetic acid/water/30% sulfuric acid (0.48 ml, 20/4/0.5 V/V/V). Mercury(II) oxide (9.6 mg) was added, and the reaction mixture was stirred for 105 minutes at 35° C. Sodium hydroxide solution was added to neutralize the reaction mixture after which water (0.4 ml) was added. The reaction mixture was extracted with methylene chloride. The organic layer was washed with water till neutral, dried and evaporated under reduced pressure to afford 70 mg of the title compound.

IR (KBr): 3485 (2x OH), 1700 (CO), 1665 (CO), 1614 (C=C).

NMR (CDCl$_3$): 0.737 (C$^{18}$H$_3$), 1.317 (C$^{19}$H$_3$), 2.27 C$^{21}$H$_3$) 3.15 (OH), 5.87 (C$^4$H).

$^{13}$C NMR (CDCl$_3$): 14.31 (C$^{18}$), 19.78 (C$^{19}$), 27.59 (C$^{21}$), 37.25 (C$^8$), 43.64 (C$^{14}$), 44.19 (C$^{10}$), 47.59 (C$^{13}$), 76.21 (C$^9$), 89.80 (C$^{17}$) 126.49 (C$^4$), 168.94 (C$^5$), 199.30 (C$^3$), 211.01 (C$^{20}$).

EXAMPLE 19

9-Alpha,17-beta-dihydroxy-17-alpha-ethynyl-16-methyleneandrost-4-en-3-one

9-Alpha-hydroxy-3-methoxy-16-methyleneandrosta-3,5-dien-17-one (1. 049 g), lithium acetylide.ethylenediamine complex (90%) (1.933 g) in dry tetrahydrofuran (10 ml) are stirred at room temperature for 20 hours. The reaction contents are then cooled and brought to pH 1.0 with 4N HCl and further stirred for 45 minutes at room temperature. Thereafter, most of the solvent mixture are evaporated under reduced pressure and the contents extracted with methylene chloride. The combined methylene chloride extracts were washed with saline and dried over anhydrous magnesium sulfate. The solvent is removed under reduced pressure and the product dried under vacuum.

Yield=0.490 g. This product has been further purified through chromatography, using toluene:acetone=2:1 as the eluent.

IR (KBr): 3609 (OH), 3403 (OH), 3251 (≡CH), 3081 (=CH$_2$), 1650 (CO), 1611 (C=C).

NMR (DMSO-d$_6$): 0.666(C$^{18}$H$_3$), 1.206(C$^{19}$H$_3$), 3.31(C≡CH), 4.11(OH) 4.93, 5.23(C=CH$_2$) 5.55(OH), 5.63(C$^4$H).

$^{13}$C-NMR (DMSO-d$_6$): 12.05(C$^{18}$), 19.54(C$^{19}$), 75.71(C$^{21}$), 108.34(methylene), 125.06(C$^4$), 75.43(C$^9$), 79.06(C$^{17}$), 86.31(C$^{20}$), 154.44(C$^{16}$), 170.88(C$^5$).

Mass spectrum m/e: 340, 322, 314.

EXAMPLE 20

17-Alpha-acetyl-9-alpha,17-beta-dihydroxyandrost-4-en-3-one

Under a nitrogen atmosphere tetrahydrofuran (12.5 ml) was added dropwise to a 15% solution of n-butyllithium in hexane (25 ml) at 15° C. in 3 minutes. After adding dropwise ethyl vinyl ether (12.5 ml) in 5 minutes, the solution was refluxed for 20 minutes, cooled to 20° C. and solid 9-alpha-hydroxy-3-methoxyandrosta-3,5-alien-17-one (1.25 g) was added. The reaction mixture was stirred for 30 minutes at 20° C. After cooling to 0° C. water (12.5 ml) was added. The organic layer was separated and washed with water. The combined aqueous layers were extracted with toluene. The organic layers were combined, washed, dried and evaporated at reduced pressure to afford an oil, which was dissolved in a mixture of methanol (5 ml) and water (1 ml). Aqueous hydrochloric acid (6N) was added till a pH of 0.7 was reached. After stirring for 10 minutes at room temperature water was added. The reaction mixture was extracted with methylene chloride, washed till neutral, dried and evaporated at reduced pressure. Chromatography (silica gel, toluene/acetone 4/1) afforded the title compound (yield 540 mg).

NMR (CDCl$_3$): 0.983 (C$^{18}$H$_3$), 1.300 (C$^{19}$H$_3$), 2.25 (C$^{21}$H$_3$), 5.78 (C$^4$H), 7.13 (OH).

IR (KBr): 3508 (OH), 3400 (OH), 1685 (CO), 1665 (CO), 1612 (C=C).

EXAMPLE 21

17-Alpha-cyano-9-alpha-hydroxy-16-beta-methyl-17-betatrimethylsilyloxyandrost -4-en-3-one Potassium cyanide (30 mg), 18-crown-6 (30 mg) and trimethylsilyl cyanide (0.48 ml; 3.6 mmol) were added to a stirred solution of 9-alpha-hydroxy-3-methoxyandrosta-3,5-dien-17-one (0.99 g; 3.0 mmol) in methylene chloride (6 ml) under a nitrogen atmosphere. The reaction mixture was stirred for 16 hours at room temperature and concentrated under reduced pressure to an oil. The oil was stirred for 3 hours in 3N aqueous hydrochloric acid (15 ml) to give a solid which was filtered, washed with water, dried and crystallized from methanol/water to give 0.92 g (71%) of the title compound.

M.p.: 211°–213° C.

NMR (CDCl$_3$): 0.25 (s,9H), 0.818 (C$^{18}$H$_3$), 1.026 (C$^{16}$H$_3$), 1.314 (C$^{19}$H$_3$), 5.87 (C$^4$H).

IR (KBr): 3415 (OH), 2225 (CN), 1675 (CO), 1615 (C=C).

EXAMPLE 22

17-Alpha-cyano-9-alpha,17-beta-dihydroxy-16-betamethylandrost-4-en-3-one

A suspension of 17-alpha-cyano-9-alpha-hydroxy-16-beta-methyl -17-beta-trimethylsilyloxyandrost-4-en-3-one (0.70 g) in 3N aqueous hydrochloric acid (28 ml) was stirred at room temperature for 48 hours. The suspension was extracted with ethyl acetate. The organic layer was washed with water and concentrated under reduced pressure. The residue was crystallized from methylene chloride/diethyl ether. The precipitate was filtered, washed with diethyl ether and dried to afford 0.40 g (71%) of the title compound.

M.p.: 270°–272° C.

NMR (CDCl$_3$+DMSO-d6): 0.838 (C$^{18}$H$_3$), 1.072 (C$^{16}$H$_3$), 1.294 (C$^{19}$H$_3$), 3.87 (OH), 5.73 (C$^4$H), 6.07 (OH).

IR (KBr): 3500 (OH), 3400 (OH), 2225 (CN), 1665 (CO).

EXAMPLE 23

17-Alpha-cyano-9-alpha,17-beta-dihydroxyandrost-4-en-3-one

Trimethylsilyl cyanide (1.6 ml; 12 mmol) was added to a stirred solution of 9-alpha-hydroxy-3-methoxyandrosta-3,5-dien-17-one (3.16 g; 10 mmol), potassium cyanide (100 mg), 18-crown-6 (100 mg) in methylene chloride (20 ml) under a nitrogen atmosphere. After stirring for 17 hours at room temperature the solvent was evaporated under reduced pressure, whereafter 3N aqueous hydrochloric acid (50 ml) was added to the residue. After stirring for a few hours the product precipitated. After 25 hours the precipitate was filtered, washed with water, dried and crystallized from ethanol-/ethyl acetate to give 1.71 g (52%) of the title compound.

M.p.: 217°–219° C.

NMR (DMSO-d6): 0.891 (C$^{18}$H$_3$), 1.316 (C$^{19}$H$_3$), 5.85 (C$^4$H)

IR (KBr): 3520 (OH), 3240 (OH), 2215 (CN), 1660 (CO).

EXAMPLE 24

17-Beta-cyano-3,3-ethylenedioxy-9-alpha,17-alphadihydroxyandrost-5-ene p-Toluenesulfonic acid monohydrate (192 mg) was added to a stirred suspension of 17-beta-cyano-9-alpha,17-alpha-dihydroxyandrost-4-en-3-one (5.0 g), trimethyl orthoformate (6.25 ml), ethylene glycol (43.75 ml) and benzene (25 ml) after which the starting material soon dissolved. The mixture was stirred at room temperature for 4 hours during which time the product precipitated.

The reaction mixture was poured into a mixture of water (50 ml), pyridine (1 ml) and diethyl ether (50 ml) after which the slurry was filtered. The crystals were washed with water and dried to give 4.5 g of the title compound.

NMR (CDCl$_3$): 0.926 (C$^{18}$H$_3$), 1.167 (C$^{19}$H$_3$), 3.94 (ethylenedioxy-H), 5.36 (C$^6$H), 5.38 (OH).

IR (KBr): 3562 (OH), 3405 (OH), 2240 (CN).

EXAMPLE 25

17-Beta-cyano-3,3-ethylenedioxy-9-alpha-hydroxy-17-alpha-(tetrahydropyran -2'-yloxy)-androst-5-ene p-Toluenesulfonic acid monohydrate (50 mg) was added to a stirred solution of 17-beta-cyano-3,3-ethylenedioxy-9-alpha, 17-alpha-dihydroxyandrost-5-ene (5.0 g) in methylene chloride (10 ml) and 2,3-dihydropyran (10 ml). After stirring for 3 hours at room temperature pyridine (2 ml) was added and the reaction mixture was poured into water. The phases were separated and the aqueous layer was extracted with methylene chloride (10 ml). The combined organic layers were dried and concentrated under reduced pressure to an oil. Crystallization of the oil from diethyl ether yielded 4.5 g of the title compound, as a mixture of two diastereomers.

M.p.: 210° C. (decomp.)

NMR (CDCl$_3$): 0.972, 0.995 (C$^{18}$H$_3$), 1.176 (C$^{19}$H$_3$), 3.58, 3.91 (2x m, 2H), 3.91 (ethylenedioxy-H), 5.01, 5.05(2x tr, 1H), 5.36 (C$^6$H).

IR (KBr): 3554 (OH), 2228 (CN).

EXAMPLE 26

3,3-Ethylenedioxy-9-alpha-hydroxy-17-alpha-(tetrahydropyran-2'-yloxy) -pregn-5-en-20-one A 5% solution of methyl lithium in diethyl ether (1.6M, 2 ml) was added dropwise to a stirred solution of 17-beta-cyano -3,3-ethylenedioxy-9-alpha-hydroxy-17-alpha(tetrahydropyran -2'-yloxy)-androst-5-ene (0.40 g) in dry tetrahydrofuran (3 ml). After stirring for 2 hours at room temperature a mixture of acetic acid (1.6 ml) and water (0.8 ml) was added. The organic phase was washed with an aqueous solution of potassium carbonate and with water, dried and concentrated under reduced pressure. The residue was crystallized from hexane/diethyl ether to afford the title compound (0.19 g) as a mixture of two diastereomers.

NMR (CDCl$_3$): 0.602 (C$^{18}$H$_3$), 1.157 (C$^{19}$H$_3$), 2.12, 2.20 (C$^{21}$H$_3$), 3.51, 3.97 (2x m, 2H), 3.97 (ethylenedioxy-H), 4.50, (tr, 1H), 5.40 (C$^6$H).

EXAMPLE 27

9-Alpha,17-alpha-dihydroxypregn-4-ene-3,20-dione

A 5% solution of methyl lithium in diethyl ether (1.6M, 2 ml) was added dropwise to a stirred solution of 17-beta-cyano-3,3-ethylenedioxy-9-alpha-hydroxy-17-alpha(tetrahydropyran-2'-yloxy) -androst-5-ene (0.40 g) in dry tetrahydrofuran (3 ml). After stirring for 2 hours at room temperature 2N aqueous hydrochloric acid (2 ml) was added and the reaction mixture was heated at 60° C. for 15 minutes. After cooling the reaction mixture was extracted with methylene chloride. The organic layer was washed with 2N sodium hydroxide solution, with water, dried and concentrated under reduced pressure to afford the title compound. NMR and IR were identical with the spectra of the product obtained in Example 18.

EXAMPLE 28

7-Beta-cyano-9-alpha,17-alpha-dihydroxy-3-methoxyandrosta-3,5-diene p-Toluenesulfonic acid monohydrate (160 mg) was added to a stirred suspension of 17-beta-cyano-9-alpha, 17-alpha-dihydroxyandrost-4-en-3-one (1.0 g) and trimethyl ortho formate (1 ml) in dioxane (15 ml) after which the starting material soon dissolved. The reaction mixture was stirred at room temperature for 3 hours during which time the product precipitated. After addition of some drops of pyridine the reaction mixture was poured into water. The precipitate was filtered, washed with water and dried to afford the title compound (0.9 g).

NMR (CDCl$_3$+DMSO-d6): 0.897 (C$^{18}$H$_3$), 1.043 (C$^{19}$H$_3$), 3.01 (OH), 3.52 (OCH$_3$), 5.13 (C$^4$H), 5.20 (C$^6$H), 6.14 (OH).

EXAMPLE 29

17-Beta-cyano-9-alpha-hydroxy-17-alpha-(tetrahydropyran-2'-yloxy) -androst-4-en-3-one p-Toluenesulfonic acid monohydrate (50 mg) was added to a stirred solution of 17-beta-cyano-9-alpha,17-alpha-dihydroxyandrost -4-en-3-one (5.0 g) in methylene chloride (12.5 ml) and 2,3-dihydropyran (10 ml). After stirring for 2 hours at room temperature the reaction mixture was poured into 1M aqueous sodium bicarbonate solution (25 ml) and extracted with isobutyl methyl ketone (50 ml). The organic layer was washed three times with water, dried and concentrated under reduced pressure to dryness. Purification by chromatography (silica gel; toluene/acetone 5–30% v/v) afforded the title compound (5.46 g: 87%), as a mixture of two diastereomers.

NMR (CDCl$_3$): delta 1.010, 1.031 (C$^{18}$H$_3$), 1.336 (C$^{19}$H$_3$), 2.42 (OH), 3.63, 3.93 (2x m, 2H), 4.98, 5.04 (2x tr, 1H), 5.85 (C$^4$H).

IR (KBr): 3410 (OH), 2235 (CN), 1665 (CO), 1615 (C=C).

EXAMPLE 30

17-Beta-cyano-9-alpha-hydroxy-3-methoxy-17-alpha-(tetrahydropyran -2'-yloxy) -androsta-3,5-diene p-Toluenesulfonic acid monohydrate (4 mg) was added to a stirred suspension of 17-beta-cyano-9-alphahydroxy -17-alpha-(tetrahydropyran-2'-yloxy)androst-4-en-3-one (0.40 g) in trimethyl orthoformate (1 ml) and methanol (2 ml). After stirring at room temperature for 10 minutes TLC showed the reaction to the enol ether to be complete. After adding a drop of pyridine the reaction mixture was concentrated under reduced pressure to afford the title compound as a glassy solid, which, without further purification, was used directly for the next step.

EXAMPLE 31

9-Alpha,17-alpha-dihydroxypregn-4-ene-3,20-dione

The crude enol ether as prepared in Example 30, was dissolved in dry tetrahydrofuran (3 ml) after which a 5% solution of methyl lithium in diethyl ether (2 ml) was added dropwise. Additional tetrahydrofuran (1 ml) was added and the reaction mixture was stirred at room temperature for 2 hours. After addition of 2N aqueous hydrochloric acid (4 ml) the reaction mixture was heated at 60° C. for 1 hour, cooled to room temperature and extracted with ethyl acetate/water. The organic phase was successively washed with water, potassium carbonate solution and water, dried and concentrated under reduced pressure to afford the title compound (0.31 g), which: was further purified by crystallization from diethyl ether. IR was identical with the spectrum of the product obtained in Example 18.

EXAMPLE 32

17-Alpha -bromoethynyl-9-alpha-hydroxy-17-betanitrooxyandrost-4-en-3-one

N-bromosuccinimide (0.22 g; 1.24 mmol) and silver nitrate (18 mg) were added to a stirred solution of 17-alphaethynyl -9-alpha-hydroxy -17-beta-nitrooxyandrost-4-en-3-one (373 mg; 1 mmol) in acetone (7 ml) at room temperature. After stirring for 30 minutes ice water was added to the reaction mixture. The resulting precipitate was filtered and solved in a mixture of ethyl acetate and methylene chloride. This organic solution was washed with water, dried and concentrated under reduced pressure to give the title compound (420 mg; yield 93%).

NMR (CDCl$_3$): 0.969 (C$^{18}$H$_3$), 1.331 (C$^{19}$H$_3$), 2.42 (OH), 5.88 (C$^4$H).

IR (KBr): 3328 (OH), 2202 (C≡C), 1664 (CO), 1630, 1.301, 1287 (ONO$_2$).

EXAMPLE 33

21-Bromo-17-alpha-formyloxy-9-alpha-hydroxypregn-4-ene-3,20-dione

To a stirred solution of 17-alpha-bromoethynyl-9-alpha-hydroxy -17-beta-nitrooxyandrost-4-en-3-one (360 mg) in formic acid (3.05 ml) and 1-methyl-pyrrolidone (0.61 ml) silver nitrate (15.3 lug) was added at room temperature. After stirring for 7 hours at room temperature the reaction mixture was poured in a mixture of ice water and methylene chloride. The organic layer was washed with water until neutral, dried and concentrated under reduced pressure to dryness. The crude product (0.50 g) was purified over silica gel with toluene/acetone 3/1 to afford 0.19 g (52%) of the title compound.

NMR (CDCl$_3$): 0.758 (C$^{18}$H$_3$), 1.337 (C$^{19}$H$_3$), 2.42 (OH), 3.98, 4.07 (C$^{21}$H$_2$), 5.89 (C$^4$H), 8.09 (formyl-H).

IR (KBr): 3400 (OH), 1720 (CO), 1636 (CO), 1150 (COC).

EXAMPLE 34

21-Bromo-9-alpha,17-alpha-dihydroxypregn-4-ene-3,20-dione

A suspension of 21-bromo-17-alpha-formyloxy-9-alpha-hydroxypregn -4-ene-3,20-dione (100 mg; 0.23 mmol) and potassium bicarbonate (78 mg) in a mixture of methanol (8.1 ml) and water (1.3 ml) was stirred at room temperature for 4 hours. After evaporating under reduced pressure of the methanol, the residue was extracted with methylene chloride and water. Re organic layer was washed with water, dried and concentrated under reduced pressure to give 93 mg of the title compound.

NMR (CDCl$_3$): 0.726 (C$^{18}$H$_3$), 1.325 (C$^{19}$H$_3$), 2.43 (OH), 4.20, 4.40 (C$^{21}$H$_2$), 5.87 (C$^4$H).

IR (KBr): 3460, 3400 (OH), 1732 (CO), 1655 (CO), 1622 (C=C).

EXAMPLE 35

21-Acetoxy-9-alpha,17-alpha-dihydroxypregn-4-ene-3,20-dione

A suspension of 21-bromo-9-alpha,17-alphadihydroxypregn -4-ene-3,20-dione (30 mg) and potassium acetate (30 mg) in acetone (0.75 ml) was heated at 60° C. for 1 hour in a sealed bottle. TLC (toluene/acetone 3/1)

showed the reaction to be complete. The reaction mixture was extracted with methylene chloride and water. The organic layer was washed with water till neutral, dried and concentrated to give the title compound (27 mg)

NMR (CDCl$_3$): 0.716 (C$^{18}$H$_3$), 1.318 (C$^{19}$H$_3$), 2.17 (COCH$_3$), 4.89, 5.05 (C$^{21}$H$_2$), 3.1 (OH), 5.86 (C$^4$H).

IR (KBr): 3470 (OH), 1750 (OCO), 1720 (CO), 1649 (CO).

EXAMPLE 36

17-Alpha-formyloxy-9-alpha-hydroxypregn-4-ene-3,20-dione and 9-alpha-hydroxypregn-4,16-diene-3,20-dione Trifluoroacetic anhydride (1.29 ml; 9.15 mmol) was added dropwise to a stirred solution of 17-alpha-ethynyl-9-alpha, 17-beta-dihydroxyandrost-4-en-3-one (1.0 g; 3.05 mmol) in dimethylformamide (10 ml) at 2° C. The reaction mixture was stirred for 10 minutes after which formic acid (10 ml) and mercury(II) acetate (0.14 g) were added. After stirring for 9 hours at 55° C. the reaction mixture was poured into water (60 ml) and extracted with methylene chloride. The organic layer was washed with water, dried and concentrated under reduced pressure. The resulting crude product was chromatographed (silica gel; toluene/acetone 4/1) to afford 2 products: 470 mg of 17-alpha-formyloxy-9-alpha-hydroxypregn-4-ene-3,20-dione.

NMR (CDCl$_3$): 0.701 (C$^{18}$H$_3$), 1.332 (C$^{19}$H$_3$), 2.09 (C$^{21}$H$_3$), 2.43 (OH), 5.89 (C$^4$H), 8.09 (formyl-H).

IR (KBr): 3400 (OH), 1730 (CO), 1651 (CO), 1620 (C=C), 1162 (COC)

and 170 mg of 9-alpha-hydroxypregna-4,16-diene-3,20-dione.

NMR (CDCl$_3$): 0.948 (C$^{18}$H$_3$), 1.347 (C$^{19}$H$_3$), 2.26 (C$^{21}$H$_3$), 2.41 (OH), 5.86 (C$^4$H), 6.73 (C$^{16}$H).

IR (KBr): 3468 (OH), 1660 (CO), 1620 (C=C), 1581 (C=C).

EXAMPLE 37

9-Alpha,17-alpha-dihydroxypregn-4-ene-3,20-dione

To a stirred solution of 17-alpha-formyloxy-9-alpha-hydroxypregn-4-ene-3,20-dione (100 mg) in a mixture of methanol (10 ml) and water (1.6 ml) potassium bicarbonate (94 mg) was added at room temperature. After stirring for 20 hours at room temperature methanol was evaporated under reduced pressure. The residue was extracted with methylene chloride and water. The organic layer was washed with water, dried and concentrated under reduced pressure to afford 80 mg (86%) of the title compound.

IR and NMR were identical with the spectra of the product obtained in Example 18.

EXAMPLE 38

3,3-Ethylenedioxy-9-alpha-hydroxyandrost-5-en-17-one

To a stirred suspension of 17-beta-cyano-3,3-ethylenedioxy-9-alpha,17-alpha-dihydroxyandrost-5-ene (0,20 g) in methanol (5 ml) 2N sodium hydroxide solution (1 ml) was added, after which a clear solution was formed. TLC indicated the reaction was complete after stirring for 10 minutes at room temperature. Water (5 ml) was added and the resulting precipitate was filtered, washed with water and dried to afford 0.11 g of the title compound.

NMR (CDCl$_3$): 0.886 (C$^{18}$H$_3$), 1.186 (C$^{19}$H$_3$), 3.94 (ethyleendioxy-H), 5.42 (C$^6$H).

IR (KBr): 3595 (OH), 1742 (CO).

EXAMPLE 39

3,3-Ethylenedioxy-17-alpha-ethynyl-9-alpha,17-betadihydroxyandrost-5-ene

A solution of 3,3-ethylenedioxy-9-alphahydroxyandrost-5-en-17-one (1.0 g) in dioxane (15 ml) was added dropwise in 10 minutes to a stirred suspension of lithium acetylide ethylenediamine complex (90%) (1.5g) in ethylenediamine (5 ml). After stirring for 4 hours at room temperature water and methylene chloride (100 ml) were added to the reaction mixture. The organic layer was washed with water until neutral, dried and concentrated under reduced pressure. The crude product (0.94g) was crystallized from hexane and methylene chloride to afford the title compound (0.59 g; 55%).

NMR (CDCl$_3$): 0.873 (C$^{18}$H$_3$), 1.175 (C$^{19}$H$_3$), 1.16 (OH), 2.60 (C$^{21}$H), 3.93 (ethylenedioxy-H), 5.40 (C$^6$H).

IR (KBr): 3580 (OH), 3480 (OH), 3270 (C≡C).

EXAMPLE 40

17-Alpha-formyloxy-9-alpha-hydroxypregn-4-ene-3,20-dione and 9-Alpha-hydroxypregn-4,16-diene-3,20-dione Trifluoroacetic anhydride(0.21 ml; 1.5 mmol) was added dropwise to a stirred solution of 3,3-ethylenedioxy-17-alpha-ethynyl -9-alpha,17-beta-dihydroxyandrost-5-ene (372 mg; 1 mmol) in dimethylformamide (3.7 ml) at 2° C. The reaction mixture was stirred for, 10 minutes after which formic acid (3.7 ml) and mercury(II) acetate (46 mg) were added. After stirring for 11 hours at 55° C. the reaction mixture was poured into ice water and extracted with methylene chloride. The organic layer was washed with water, dried and concentrated under reduced pressure. The resulting crude product was chromatographed (silica gel; toluene/acetone 3/1) to afford 150 mg of 17-alpha-formyloxy-9-alpha-hydroxypregn-4-ene-3,20-dione and 60 mg of 9-alpha-hydroxypregna-4,16-diene-3,20-dione.

IR and NMR of both products were identical with the spectra of the products obtained in Example 36.

EXAMPLE 41

17-Alpha-chloroethynyl-9-alpha,17-beta-dihydroxyandrost-4-en-3-one

A solution of 1,2-trans-dichloro-ethene (3.1 ml) in anhydrous diethyl ether (10 ml) was added dropwise to a stirred solution of n-butyl lithium (1.6M) in hexane. (50 ml) at −5° C. under a nitrogen atmosphere after which the temperature was allowed to raise to 20° C. A solution of 9-alpha-hydroxy -3-methoxyandrosta-3,5-dien-17-one (3.10 g) in anhydrous toluene (70 ml) then was added dropwise in 20 minutes. After stirring for 90 minutes at reflux temperature the reaction mixture was allowed to stand at room temperature for 16 hours. The reaction mixture was poured into water. The aqueous phase was extracted with ethyl acetate. The combined organic layers were washed with water till neutral, dried and concentrated under reduced pressure to dryness (4.0 g). The residue was dissolved in a mixture of methanol (100 ml), water (10 ml) and 6N aqueous hydrochloric acid (2 ml). After stirring for 15 minutes at room temperature the mixture was concentrated under reduced pressure. The residue was extracted in methylene chloride/water, after which the organic phase was washed with water, dried and concentrated under reduced pressure. Purification of the residue by chromatography (silica gel, toluene/acetone 3/1) afforded the title compound (560 mg).

NMR (CDCl$_3$): 0.897 (C$^{18}$H$_3$), 1.330 (C$^{19}$H$_3$), 2.43 (OH), 5.87 (C$^4$H).

IR (KBr): 3507 (OH), 3377 (OH), 2218 (C≡C), 1642 (CO), 1608 (C=C).

EXAMPLE 42

17-Alpha-chloroethynyl-9-alpha-hydroxy-17-betanitrooxyandrost-4-en-3-one

The title compound was prepared according the process as described in Example 16, starting from 17-alpha-chloroethynyl -9-alpha,17-beta-dihydroxyandrost-4-en-3-one (560 mg), acetic anhydride (4.7 ml) and fumic nitric acid (0.64 ml). Yield 520 mg (84%).

NMR (CDCl$_3$): 0.967 (C$^{18}$H$_3$), 1.332 (C$^{19}$H$_3$), 2.42 (OH), 5.88 (C$^4$H).

IR (KBr): 3415 (OH), 2221 (C≡C), 1660 (CO), 1626, 1298, 1284 (ONO$_2$).

EXAMPLE 43

21-Chloro-17-alpha-formyloxy-9-alpha-hydroxypregn-4-ene-3,20-dione

The title compound was prepared according the process as described in Example 33, starting from 17-alpha-chloroethynyl -9-alpha-hydroxy-17-beta-nitrooxyandrost-4-en-3-one (0.45 g), formic acid (4.2 ml), 1-methyl-pyrrolidone (0.84 ml) and silver nitrate (21 mg). Yield 0.20 g.

NMR (CDCl$_3$): 0.743 (C$^{18}$H$_3$), 1.334 (C$^{19}$H$_3$), 2.42 (OH), 4.14, 4.25 (2 x d; C$^{21}$H$_2$), 5.88 (C$^4$H).

IR (KBr): 3400 (OH), 1740 (CO), 1725 (CO), 1625 (CO), 1150 (COC).

EXAMPLE 44

17-Alpha-acetoxy-17-beta-ethynyl-9-alpha-hydroxyandrost-4-en-3-one

A mixture of 17-beta-ethynyl-9-alpha,17-alpha. dihydroxyandrost-4-en-3-one (1.0 g), acetic anhydride (1 ml), triethylamine (1 ml), 4-dimethylaminopyridine (57 mg) and toluene (2.5 ml) was heated at 90° C. for 11 hours in a sealed bottle. The cooled reaction mixture was extracted with a mixture of methylene chloride and water. The organic layer was washed successively with 1N aqueous hydrochloric acid, 1N aqueous sodium hydroxide and water. After concentrating under reduced pressure the crude product was purified by chromatography (silic gel, toluene/acetone 3/1) to afford 310 mg of the title compound.

NMR (CDCl$_3$): 0.973 (C$^{18}$H$_3$), 1.344 (C$^{19}$H$_3$), 2.04 (COCH$_3$), 2.43 (OH), 2.58 (C$^{21}$H), 5.87 (C$^4$H).

IR (KBr): 3380 (OH), 3310 (≡CH), 1748 (CO), 1655 (CO), 1620 (C=C).

EXAMPLE 45

17-Alpha-acetoxy-21,21-diiodo-9-alpha-hydroxypregn-4-ene-3,20-dione

A mixture of 40% peracetic acid (0.14 ml), acetic acid (8.3 ml) and water (1.0 ml) was added dropwise in 10 minutes to a stirred mixture of 17-alpha-acetoxy-17-betaethynyl -9-alpha-hydroxyandrost-4-en-3-one (310 mg), iodine (212 mg), acetic acid (2.3 ml) and water 0.3 ml). After stirring for 2 hours at room temperature the reaction mixture was poured into water (80 ml) and the resulting precipitate was filtered and dissolved in methylene chloride. The solution was washed successively with a 7% aqueous potassium iodide solution, a 10% aqueous sodium thiosulfate solution and water, dried and concentrated under reduced pressure to give 0.30 g of the title compound. The first aqueous filtrate was extracted with methylene chloride after which the organic phase was washed according to the same procedure as described, dried and evaporated under reduced pressure to give an additional 0.21 g of the title compound.

NMR (CDCl$_3$): 0.874 (C$^{18}$H$_3$), 1.336 (C$^{19}$H$_3$), 2.13 (COCH$_3$), 2.43 (OH), 5.53 (C$^{21}$H), 5.89 (C$^4$H).

IR (KBr): 3513 (OH), 1725 (CO), 1650 (CO), 1250 (COC).

EXAMPLE 46

9-Alpha-hydroxy-3-(N-pyrrolidinyl) androsta-3,5-dien-17-one

Under a nitrogen atmosphere pyrrolidine (0.4 ml) was added to a stirred solution of 9-alpha-hydroxyandrosta-4-ene -3,17-dione (1.0 g) in methanol (4 ml) and methylene chloride (1 ml). Shortly thereafter the product precipitated. After cooling to 5° C. the mixture was filtered, washed with methanol and dried to afford 0.88 g of the title compound.

Yield 75%.

M.p. 176°–183° C. (decomp.).

NMR (CDCl$_3$): 0.902 (C$^{18}$H$_3$), 1.148 (C$^{19}$H$_3$), 3.16 (NCH$_2$, m, 4H), 4.79 (C$^4$H), 5.10 (C$^6$H).

IR (KBr): 3495 (OH), 1735 (CO), 1630 (C=C), 1595 (C=C).

EXAMPLE 47

20-Acetylimino-3,3-ethylenedioxy-9-alpha-hydroxy-17-alpha-(tetrahydropyran -2'-yloxy)-pregn-5-ene A 5% solution of methyl lithium in diethyl ether (1.6M, 4 ml) was added dropwise to a stirred solution of 17-beta-cyano -3,3-ethylenedioxy-9-alpha-hydroxy-17-alpha-(tetrahydropyran -2'-yloxy)-androst-5-ene (0.80 g) in dry tetrahydrofuran. After stirring for 2 hours at room temperature a mixture of acetic anhydride (1.5 ml) and tetrahydrofuran (1.5 ml) was added. The reaction mixture was allowed to stand at room temperature for 16 hours. The reaction mixture was then poured into an aqueous sodium bicarbonate solution and extracted with ethyl acetate. The organic layer was washed with water, dried and concentrated under reduced pressure to dryness. The crude product (1.0 g) was purified by chromatography (silica gel; toluene/acetone 2/1) to afford the title compound.

NMR (CDCl$_3$): 0.720 (C$^{18}$H$_3$), 1.164 (C$^{19}$H$_3$), 1.930 (COCH$_3$), 2.138 (CH$_3$), 3.53, 3.93 (2x m, 2H), 3.93 (ethylenedioxy-H), 4.65 (tr, 1H), 5.38 (C$^6$H).

EXAMPLE 48

20-Acetylamino-3,3-ethylenedioxy-9-alpha-hydroxy-17-alpha-(tetrahydropyran -2'-yloxy)-pregna-5,20-diene 20-Acetylimino-3,3-ethylenedioxy-9-alpha-hydroxy-17-alpha-(tetrahydropyran -2'-yloxy) -pregn-5-ene was prepared according to the previous example. The crude product was solved in acetic acid and stirred for 1.5 hours at room temperature. After addition of toluene the reaction mixture was concentrated under reduced pressure. Again toluene was added and the solution was concentrated under reduced pressure to give an oil (0.96 g) which was purified by chromatography (silica gel, toluene/ethyl acetate 1/2) to afford the title compound.

NMR (CDCl$_3$): 0.680 (C$^{18}$H$_3$), 1.161 (C$^{19}$H$_3$), 2.02 (COCH$_3$), 3.55, 3.93 (2 x m, 2H), 3.93 (ethylenedioxy-H), 4.74 (tr, 1H), 4.89, 6.12 (=CH$_2$, 2 x s, 2H), 5.39 (C$^6$H), 6.93 (NH).

The product was hydrolysed under mild conditions to 3,3-ethylenedioxy-9-alpha-hydroxy-17-alpha-(tetrahydropyran-2-yloxy)-pregn-5-en-20-one.

NMR was identical with the spectrum of the product obtained according to Example 26.

EXAMPLE 49

17-Alpha-hydroxy-pregna-4,9(11)-diene-3,20-dione 3,3-Ethylenedioxy-9-alpha-hydroxy-17-alpha(tetrahydropyran-2'-yloxy)-pregn-5-en-20-one (50 mg) was added to a 70% aqueous sulfuric acid solution (0.6 ml). After stirring for one hour at room temperature the reaction mixture was added dropwise into water and extracted with ethyl acetate. The organic layer was washed with an aqueous potassium carbonate solution, with water, dried and evaporated under reduced pressure to afford the title compound (18 mg).

NMR (CDCl$_3$): 0.725 (C$^{18}$H$_3$), 1.341 (C$^{19}$H$_3$), 2.04 (C$^{21}$H$_3$), 5.54 (C$^{11}$H), 5.76 (C$^4$H).

EXAMPLE 50

17-Alpha-hydroxypregna-4,9(11)-diene-3,20-dione

9-Alpha,17-alpha-dihydroxypregn-4-ene-3,20-dione (50 mg) was added to a 70% aqueous sulfuric acid solution (1.5 ml). After stirring for 40 minutes at room temperature the reaction mixture was poured into ice water and extracted with methylene chloride. The organic layer was washed with water till neutral, dried and concentrated under reduced pressure to give the title compound (37 g).

NMR was identical with that of the product obtained in Example 49.

EXAMPLE 51

17-Alpha-(1'-butoxyethoxy)-17-beta-cyano-3,3-ethylenedioxy-9-alpha-hydroxyandrost-5-ene p-Toluenesulfonic acid monohydrate (250 mg) was added to a stirred suspension of 17-beta-cyano-3,3-ethylenedioxy -9-alpha,17-alpha-dihydroxyandrost-5-ene (5.0 g) in butyl vinyl ether (3.75 ml) and methylene chloride (50 ml), after which a clear solution was formed. The reaction mixture was stirred for 1 hour at room temperature, after which additional butyl vinyl ether (3.75 ml) was added. After stirring for 45 minutes at room temperature additional methylene chloride (150 ml) was added and the reaction mixture was extracted with 1M aqueous sodium bicarbonate and three times with water. The organic phase is dried and concentrated under reduced pressure. Purification by chromatography (silica gel; toluene/acetone 7-25% v/v) afforded the title compound, as a mixture of diastereomers.

NMR (CDCl$_3$): 0.917 (butyl-CH$_3$), 0.957, 0.971 (C$^{18}$H$_3$), 1.163 (C$^{19}$H$_3$), 1.34, 1.37 (2x d,3H), 3.922 (ethylenedioxy H), 5.00, 5.09 (2x m, 1H), 5.37 (C$^6$H).

EXAMPLE 52

9-Alpha,17-alpha-dihydroxypregn-4-ene-3,20-dione

17-Beta-cyano-3,3-ethylenedioxy-9-alpha,17-alphadihydroxyandrost -5-ene(0.40 g) was converted into 17-alpha-(1'-butoxyethoxy) -17-beta-cyano-3,3-ethylenedioxy-9-alphahydroxyandrost-5-ene according to the previous example. The crude reaction product was dissolved in dry tetrahydrofuran (3 ml) after which a 5% solution of methyl lithium in diethyl ether (1.6M, 2 ml) was added dropwise to the stirred solution. After stirring for 2 hours at room temperature 2N aqueous hydrochloric acid (2 ml) was added and the reaction mixture was heated at 60° C. for 1 hour. After cooling the reaction mixture was extracted with ethyl acetate. The organic layer was washed with an aqueous sodium bicarbonate solution and water, dried and evaporated under reduced pressure to afford the title compound (0.34 g) which was further purified by crystallization from diethyl ether. IR was identical with the spectrum of the product obtained in Example 18.

EXAMPLE 53

9-Alpha,17-alpha-dihydroxy-21-iodopregn-4-ene-3,20-dione

A mixture of 9-alpha,17-alpha-dihydroxypregn-4-ene-3,20-dione (100 mg), calcium oxide (150 mg), iodine (150 mg), methanol (0.45 ml) and dry tetrahydrofuran (0.75 ml) was stirred for 20 hours at room temperature. After addition of ethyl acetate, the reaction mixture is filtered, washed successively with a 10% sodium iodide solution, twice with a sodium thiosulfate solution and four times with water. The organic phase was dried and concentrated under reduced pressure at room temperature to afford the title compound (99 mg) which, without purification, was used for the next step.

EXAMPLE 54

21-Acetoxy-9-alpha,17-alpha-dihydroxypregn-4-ene-3,20-dione

9-Alpha,17-alpha-dihydroxy-21-iodopregn-4-ene-3,20-dione (99 mg), as prepared according to the previous example was dissolved in dry acetone (2.5 ml) and refluxed for 2 hours with anhydrous potassium acetate (250 mg) after which the reaction mixture was allowed to stand for 16 hours at room temperature. After addition of water the reaction mixture was extracted with ethyl acetate. The organic phase was washed with water, dried and concentrated under reduced pressure to give the title compound (77 mg). IR and NMR were identical with the spectra of the product obtained according to Example 35.

EXAMPLE 55

17-Alpha-(1'-ethoxyethenyl)-9-alpha,17-beta-dihydroxy-3-methoxy-androsta-3,5-diene Example 20 was repeated, however, the intermediate ethoxyethenyl derivative was not hydrolysed but isolated and identified by NMR. The reaction mixture was extracted with water, after which the organic phase was concentrated under reduced pressure at a temperature below 40° C. Additional hexane was added and the organic phase was further concentrated under reduced pressure till the product precipitated. The crystals were filtered, washed with hexane and dried to afford the title compound.

NMR (CDCl$_3$): 0.937 (C$^{18}$H$_3$), 1.098 (C$^{19}$H$_3$), 1.29 (CH$_3$), 3.56 (OCH$_3$), 3.75 (OCH$_2$), 4.06, 4.18 (=CH$_2$, 2 x d), 5.16 (C$^4$H), 5.29 (C$^6$H).

EXAMPLE 56

17-Alpha-acetyl-9-alpha,17-beta-dihydroxy-16-methyleneandrost-4-en-3-one

The title compound was prepared according the process as described in Example 20, starting from 9-alphahydroxy -3-methoxy-16-methylene-androsta-3,5-dien-17-one (1.25 g). The crude product (0.83 g) was further purified by chromatography (silicagel, toluene-/acetone 3/1) to yield 0.25 g.

NMR (CDCl$_3$): 0.938 (C$^{18}$H$_3$), 1.337 (C$^{19}$[-I3), 2.28 (COCH$_3$), 2.40 (OH), 3.62 (OH), 5.17 (=CH$_2$), 5.88 (C$^4$H).

IR (KBr): 3439 (OH), 3380 (OH), 3073 (=CH$_2$), 1685 (CO), 1650 (CO), 1613 (C=C).

EXAMPLE 57

17-Alpha-ethynyl -9-alpha,17-beta-dihydroxy-16-methylene-androst-4-en-3-one

The process of Example 19 was repeated except that a mixture of 9-alpha-hydroxy-3-methoxy-16-methylene-androsta-3,5-dien-17-one (3.28 g), lithium acetylide.ethylenediamine complex (90%) (5.09 g), ethylenediamine (15 ml) and dry tetrahydrofuran (20 ml) was stirred at room temperature for 4 hours. Yield 2.96 g.

IR and NMR were identical with the product obtained in Example 19.

EXAMPLE 58

17-Alpha-formyloxy-9-alpha-hydroxy-16-methylene-pregn-4-ene-3,20-dione

Trifluoroacetic anhydride (0.35 ml) was added dropwise to a stirred solution of 17-alpha-ethynyl-9-alpha, 17-beta-dihydroxy-16-methylene-androst-4-en-3-one (525 mg) in dimethylformamide (5 ml) at 2° C. The reaction mixture was stirred for 10 minutes after which formic acid (6 ml) and mercury(II) acetate (75 mg) were added. After stirring for 7.5 hours at 60° C. the reaction mixture was poured into water and extracted with methylene chloride. The organic layer was washed with water, dried and concentrated under reduced pressure to give an oil (700 mg) which, according to TLC, was a mixture of products. Chromatography (silicagel, toluene/acetone 9/1) afforded the title compound (110 mg).

IR (CDCl$_3$): 0.916 (C$^{18}$H$_3$), 1.310 (C$^{19}$H$_3$), 2.14 (C$^{21}$H$_3$), 5.31, 5.43 (=CH$_2$, 2 x s, 2H), 5.86 (C$^4$H).

Of a second, less polar product 120 mg was obtained. It appeared to be 16-formyloxymethyl-9-alpha-hydroxypregna -4,16-diene-3,20-dione.

NMR (CDCl$_3$): 1.075 (C$^{18}$H$_3$), 1.353 (C$^{19}$H$_3$), 2.29 (C$^{21}$H$_3$), 2.41 (OH), 5.03 (CH$_{20}$), 5.88 (C$^4$H), 8.11 (formyl-H).

EXAMPLE 59

17-Alpha-ethynyl-9-alpha,17-beta-dihydroxy-16-betamethylandrost -4-en-3-one and
17-alpha-ethynyl-9-alpha, 17-beta-dihydroxy -16-alpha-methylandrost-4-en-3-one A suspension of powdered potassium hydroxide (1.8 g), tetrahydrofuran (45 ml) and ethanol (0.4 ml) was stirred at 40° C. for 30 minutes under a nitrogen atmosphere and then cooled to −40° C. 9-Alpha-hydroxy-3-methoxy-16-betamethylandrosta -3,5-dien-17-one was added portionwise after which, maintaining the temperature at −40° C., the mixture was saturated with acetylene. After the addition of dimethylformamide (2 ml) the reaction mixture was stirred at 0° C. for 1.5 hours. At a temperature of 0° C. 4N aqueous hydrochloric acid was added till a pH of 1.0 was reached, after which the reaction mixture was stirred at 45° C. till TLC indicated the deprotection of the enol ether to the 3-keto-4,5-dehydro function to be complete. Most of tetrahydrofuran was removed under reduced pressure after which the reaction mixture was extracted with water/chloroform. The organic phase was washed with brine and water, dried and concentrated under reduced pressure to dryness. Further purification of the crude product (2.0 g) from methylene chloride/hexane 1/1 afforded a 1:1 mixture of the two epimers of the title compounds.

NMR (CDCl$_3$): 0.883 (C$^{18}$H$_3$(16-beta-methyl)), 0.958 (c$^{18}$H$_3$(16-alpha-methyl)), 1.10 (beta-CH$_3$), 1.18 (alpha-CH$_3$), 1.329 (C$^{19}$H$_3$), 1.57 (OH), 2.43 (OH), 2.59 (C$^{21}$H), 2.67 (C$^{21}$H), 5.87 (C$^4$H).

IR (KBr): 3619 (OH), 3420 (OH), 3250 (=CH), 2102 (C=C), 1650 (CO), 1619 (C=C).

Mass spectrum m/e: 342.

EXAMPLE 60

17-Alpha-ethynyl-9-alpha,17-beta-dihydroxy-16-betamethylandrost-4-en-3-one

The process of example 19 was repeated except that a mixture of 9-alpha-hydroxy-3-methoxy-16-betamethylandrosta-3,5-dien-17-one (1.16 g), lithium acetylide-.ethylene-diamine complex (90%) (1.77 g), ethylenediamine (5.3 ml) and dry tetrahydrofuran (7 ml) was stirred for 4 hours at room temperature. NMR of the crude product (1.13 g) indicated the reaction to be not complete but confirmed the formation of the title compound and excluded the formation of the 16-alpha-epimer of the title compound.

NMR (CDCl$_3$): 0.883 (C$^{18}$H$_3$), 1.10 (CH$_3$), 1.329 (C$^{19}$H$_3$), 1.57 (OH), 2.43 (OH), 2.59 C$^{21}$H), 5.87 (C$^4$H).

EXAMPLE 61

17-Beta-cyano-9-alpha,17-alpha-dihydroxy-3 methoxy-16-betamethylandrosta-3,5-diene Acetic acid (3.1 ml) was added dropwise to a stirred suspension of 9-alpha-hydroxy-3-methoxy-16-betamethylandrosta -3,5-dien-17-one (9.0 g) and potassium cyanide (9 g) in methanol (72 ml) at 0° C. After stirring for 6 days the reaction mixture was concentrated under reduced pressure to dryness. The residue was stirred in 3N aqueous hydrochloric acid (350 ml) for 5 minutes, filtered, washed with water till neutral and dried in vacuo to afford 8.40 g of the title compound.

EXAMPLE 62

7-Beta-cyano-9-alpha,17-alpha-dihydroxy-16-betamethylandrost-4-en-3-one

The reaction product of Example 61 was stirred in 3N aqueous hydrochloric acid (330 ml) for 2.5 hours, The reaction mixture was extracted with ethyl acetate, after which the organic phase was washed 5 times with water, and concentrated under reduced pressure to 100 ml. The resulting precipitate was filtered, washed with ethyl acetate and dried to afford the title compound (6.84 g).

NMR was identical with the spectrum of the product obtained according to Example 10.

EXAMPLE 63

17-Beta-cyano-3,3-ethylenedithio-9-alpha,17-alpha-dihydroxy-16-beta-methylandrost-4-ene To a stirred suspension of 17-beta-cyano-9-alpha,17-alpha-dihydroxy-16-beta-methylandrost-4-en-17-one (1.60 g) in acetic acid (16 ml) ethanedithiol (0.8 ml) and boron trifluoride etherate (1.6 ml) were added after which the starting material soon dissolved. The reaction mixture was stirred at 25° C. for 15 minutes and concentrated under reduced pressure till the product precipitated. After addition of water (48 ml) the reaction mixture was stirred for 10 minutes and filtered. The product was washed with water and dried to afford the title compound (1.92 g) which was crystallized from diethyl ether containing a drop of acetic acid (yield 1.61 g).

IR (KBr): 3580 (OH), 3365 (OH), 2225 (CN), 1645 (C=C).

EXAMPLE 64

17-Alpha-(1'-butoxyethoxy)-17-beta-cyano-3,3-ethylenedithio-9-alpha-hydroxy-16-beta-methylandrost-4-ene A 0.5% w/v solution of p-toluenesulfonic acid monohydrate in diethyl ether (0.1 ml) was added to a stirred suspension of 17-beta-cyano-3,3-ethylenedithio-9-alpha,17-alpha-dihydroxy -16-beta-methylandrost-4-ene (100 mg) in a mixture of butyl vinyl ether (2 ml) and toluene (3 ml) after which the starting material soon dissolved. After stirring for 30 minutes at room temperature TLC indicated the reaction to be complete. After addition of one drop of pyridine the reaction mixture was concentrated under reduced pressure to dryness. The residue was crystallized from hexane to afford the title compound (39 mg) as a mixture of two diastereomers.

IR (KBr): 3525 (OH), 2235 (CN), 1645 (C=C).

NMR (CDCl$_3$): 0.916, 0.923 (butyl-CH$_3$; 2 x tr, 3H), 0.9666, 0.977 (C$^{18}$H$_3$, 2 x s), 1.176 (C$^{19}$H$_3$), 1.29, 1.30 (OCCH$_3$, 2 x d, 3H), 1.31 (C$^{16}$H$_3$), 5.00, 5.04 (OCHO, 2 x q, 1H), 5.79 (C$^4$H), 3.1–3.7 (ethylenedithio-H, m, 4H).

EXAMPLE 65

17-Alpha-ethynyl-9-alpha,17-beta-dihydroxy-3-methoxyandrosta-3,5-diene

A solution of 9-alpha-hydroxy-3-methoxy-androsta-3,5-dien-17-one (3.16 g) in dry tetrahydrofuran (25 ml) was added dropwise to a stirred solution of lithium acetylide.ethylenediamine complex (90%) (5.11 g) in ethylenediamine (15 ml) at 5° C. The reaction mixture was stirred for 2.5 hours at room temperature after which TLC indicated the reaction to be complete. The reaction mixture was poured into ice water and extracted with methylene chloride. The organic layer was washed with water till neutral, dried and concentrated under reduced pressure to afford the title compound (4.0 g) which, without purification, was used for the next step.

EXAMPLE 66

17-Alpha-ethynyl-9-alpha-hydroxy-3-methoxy-17-betamethylsulfonyloxy-androsta-3,5-diene A mixture of 17-alpha-ethynyl-9-alpha-17-betadihydroxy -3-methoxyandrosta-3,5-diene (4.0 g), as prepared according to the previous example, anhydrous lithium bromide (0.87 g) and anhydrous tetrahydrofuran (35 ml) was cooled to −60° C. After addition of a 15% solution of n-butyllithium in hexane (7 ml) the reaction mixture was stirred for 45 minutes at −60° C. Then methylsulfonyl chloride (0.77 ml) was added and the reaction mixture was stirred for 45 minutes at −60° C. The reaction mixture was poured into an aqueous ammonium chloride solution and extracted twice with methylene chloride. The combined organic layers were dried and, after the addition of pyridine (1 ml), concentrated under reduced pressure at 0° C. The crude product was washed with diethyl ether and filtered to afford the title compound (2.0 g) which was used, without further purification, for the next step.

EXAMPLE 67

17-Beta-ethynyl-9-alpha,17-alpha-dihydroxyandrost-4-en-3-one

17-Alpha-ethynyl-9-alpha-hydroxy-17-betamethyl-sulfonyloxy androsta-3,5-diene (2.0 g), as prepared according to the previous example, was dissolved in tetrahydrofuran (15 ml). After the addition of water (2.5 ml) and silver nitrate (150 mg) the reaction mixture was stirred for 2 hours at room temperature. The reaction mixture was poured into an aqueous ammonium chloride solution (100 ml), containing sodium cyanide (1 g), and extracted twice with methylene chloride. The combined organic layers were washed with water till neutral and concentrated under reduced pressure. The residue was dissolved in methanol (50 ml) after which water (5 ml) and 4N aqueous hyrochloric acid (2 ml) were added. After stirring for 15 minutes at room temperature the reaction mixture was concentrated under reduced pressure. The residue was dissolved in methylene chloride, washed with water, dried and concentrated under reduced pressure to afford the crude title compound (1.07 g).

NMR was identical with the spectrum of the product obtained in Example 17.

EXAMPLE 68

17-Ethynyl-9-alpha-hydroxyandrosta-4,16-dien-3-one

Phosphorus oxychloride (1.25 ml) was added to a stirred solution of 17-alpha-ethynyl-9-alpha,17-betadihydroxyandrost -4-en-3-one (0.25 g) in pyridine (2.5 ml). After refluxing for 10 minutes the reaction mixture was poured into ice water and extracted with methylene chloride. The organic layer was washed with an aqueous potassium carbonate solution and with water, dried and concentrated under reduced pressure to dryness. The crude product (0.10 g) was purified by chromatography (silica gel, toluene/acetone 9/1) to afford the title compound.

NMR (CDCl$_3$): 0.916 (C$^{18}$H$_3$), 1.350 (C$^{19}$H$_3$), 2.36 (C$^{21}$H), 5.88 (C$^4$H), 6.13 (C$^{16}$H).

EXAMPLE 69

21-Acetoxy-17-alpha-hydroxypregna-4,9(11)-dien-3,20-dione

21-Acetoxy-9-alpha,17-alpha-dihydroxypregn-4-en-3,20 dione (40 mg) was added to a 70% aqueous sulfuric acid solution (1.2 ml). After stirring for 45 minutes at room temperature the reaction mixture was poured into ice water and extracted with methylene chloride. The organic layer was washed with water, an aqueous sodium bicarbonate solution, water again, dried and concentrated under reduced pressure to afford 25 mg of solid product. NMR analysis of this crude product proved the title compound to be the main product.

NMR (CDCl$_3$): 0.655 (C$^{18}$H$_3$), 1.337 (C$^{19}$H$_3$), 2.17 (COCH$_3$) 4.85, 5.09 (2 x d, C$^{21}$H$_2$), 5.56 (C$^{11}$H), 5.76 (C$^4$H).

We claim:

1. 17-Beta-cyano-9-alpha,17-alpha-dihydroxy-16-R-androst-4-en-3-one, where R is hydrogen, hydroxy, alphamethyl, beta-methyl or methylene.

2. 17-Alpha-cyano-9-alpha,17-beta-dihydroxy-16-R-androst-4-en-3-one, where R is hydrogen, hydroxy, alphamethyl, beta-methyl or methylene.

3. 17-Alpha-haloethynyl-9-alpha,17-beta-dihydroxy-16-R-androst-4-en-3-one, where halo is chlorine or bromine and R is hydrogen, hydroxy, alpha-methyl, beta-methyl or methylene.

4. 17-Alpha-(1'-ethoxyethenyl)-3-methoxy-16-R-androsta-3,5-diene-9-alpha, 17-beta-diol where R is hydrogen, hydroxy, alpha-methyl, beta-methyl or methylene.

5. 17β-Cyano-9α,17α-dihydroxyandrost-4-en-3-one.

* * * * *